United States Patent [19]

Chapman et al.

[11] Patent Number: 5,122,146
[45] Date of Patent: Jun. 16, 1992

[54] APPARATUS FOR REDUCING A FRACTURE

[75] Inventors: Michael W. Chapman, Sacramento, Calif.; Dana C. Mears, Pittsburgh, Pa.; Charles C. Edwards, Baltimore, Md.

[73] Assignee: Pfizer Hospital Products Group, Inc., New York, N.Y.

[21] Appl. No.: 152,172

[22] Filed: Feb. 4, 1988

[51] Int. Cl.⁵ .............................................. A61B 17/56
[52] U.S. Cl. ...................................... 606/102; 606/67
[58] Field of Search .......... 128/92 R, 92 VD, 92 VK, 128/92 V, 92 VT, 92 VW, 303 R, 361, 774; 33/143 C, 511, 512, 832, 836; 606/96, 99, 102, 104

[56] References Cited

U.S. PATENT DOCUMENTS

| | | | |
|---|---|---|---|
| 2,235,419 | 3/1941 | Callahan et al. | 606/96 |
| 2,650,435 | 9/1953 | Kidd | 33/836 |
| 2,716,406 | 8/1955 | Reymann et al. | 128/92 YK |
| 3,486,500 | 12/1969 | Ball et al. | 128/92 YK |
| 4,103,683 | 8/1978 | Neufeld . | |
| 4,121,572 | 10/1978 | Krzeminski | 33/836 |
| 4,341,206 | 7/1982 | Perrett et al. | 128/92 VD |
| 4,465,065 | 8/1984 | Gotfried | 128/92 VD |
| 4,800,873 | 1/1989 | Audell | 606/62 |

FOREIGN PATENT DOCUMENTS 0187283  7/1986  European Pat. Off. ...... 128/92 VD
8504092  9/1985  PCT Int'l Appl. ........... 128/92 VD

*Primary Examiner*—Robert A. Hafer
*Assistant Examiner*—Kevin G. Rooney
*Attorney, Agent, or Firm*—Pennie & Edmonds

[57] ABSTRACT

Fracture reduction tool is disclosed for use with a guide wire for reducing a bone fracture. The guide wire is of a uniform diameter and has a beaded end for placement into the medullary canal. The tool includes an elongated hollow shaft which can be passed into the medullary canal of the fractured bone through an entry hole prepared in the bone. The shaft has a bore along its length through which the guide wire can selectively pass. The shaft and/or the guide wire can be manipulated into and within the respective medullary canal portions of the fractured bone by translational and/or rotational movements so as to reduce the fracture. The tool also includes a measurement sleeve which moves over the shaft and provides a determination of the length of a nail to be inserted into the medullary canal of the reduced bone. A handle for the proximal end of the shaft allows for ease in manipulation of the shaft and guide wire. Locking mechanisms to secure the measurement sleeve and guide wire in position relative to the shaft are also provided.

A method of operation with the fracture reduction tool of the present invention is also disclosed.

47 Claims, 21 Drawing Sheets

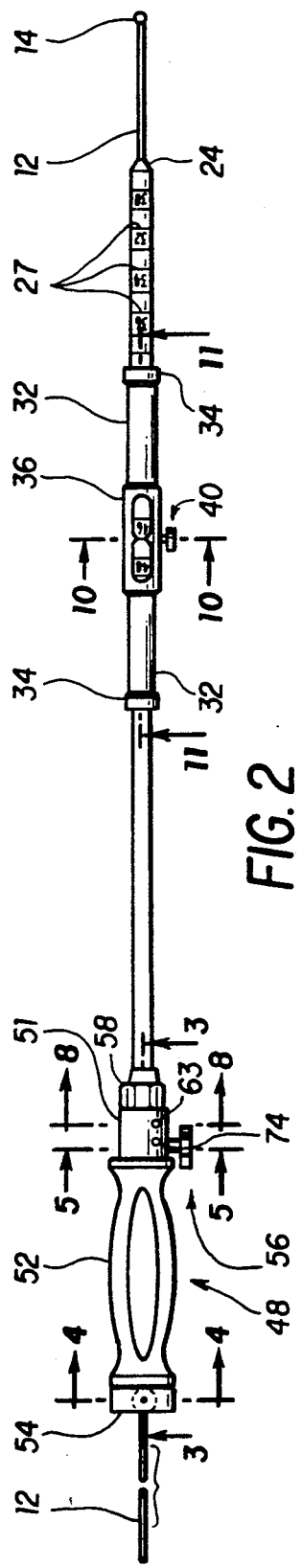
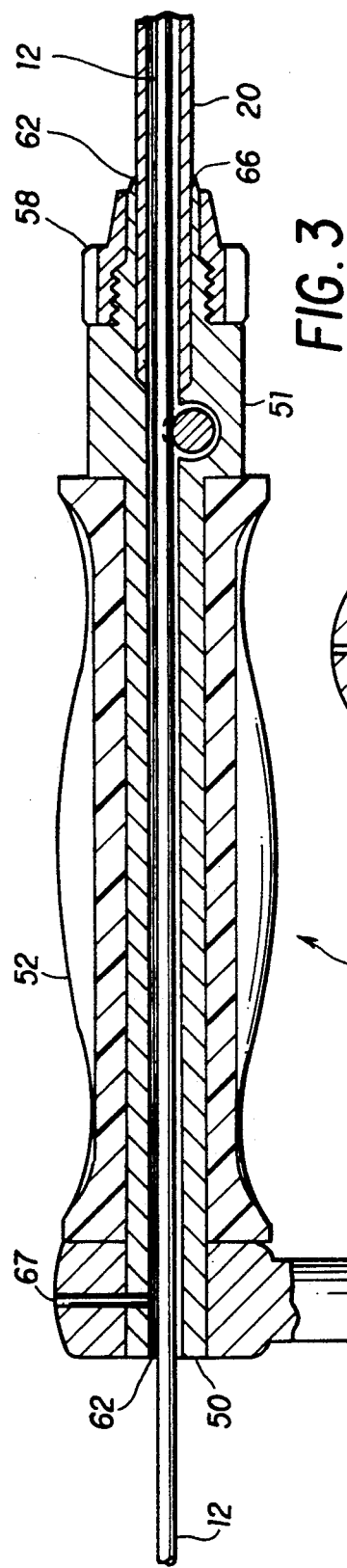
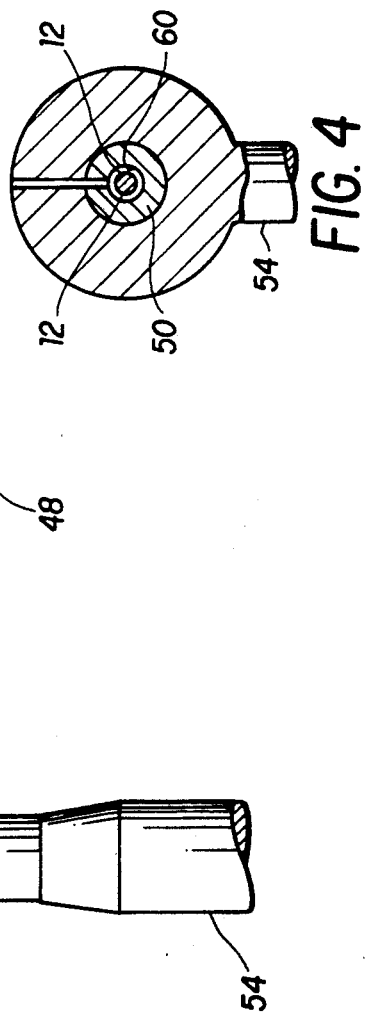

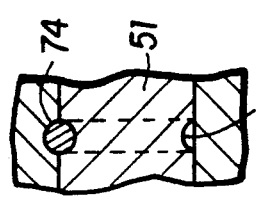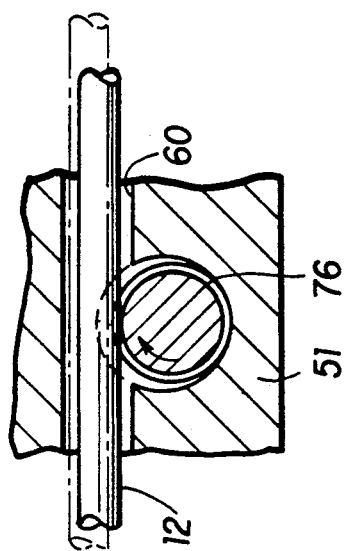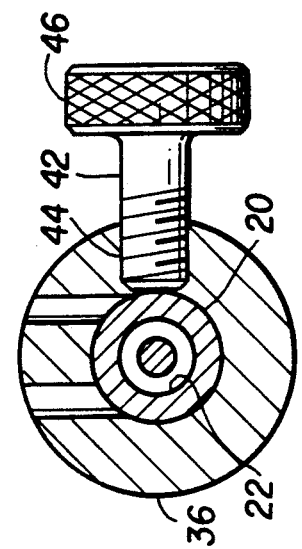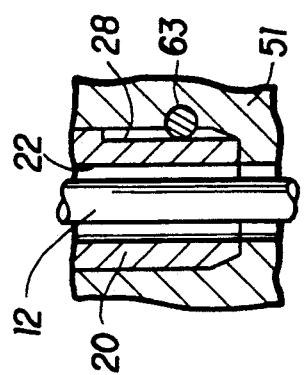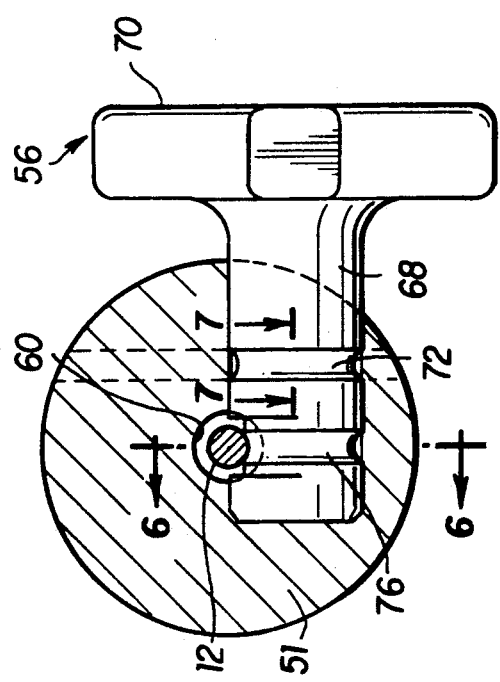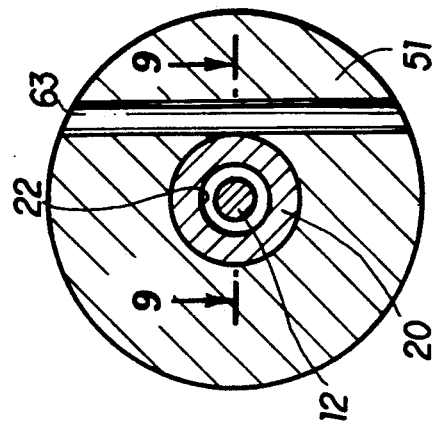

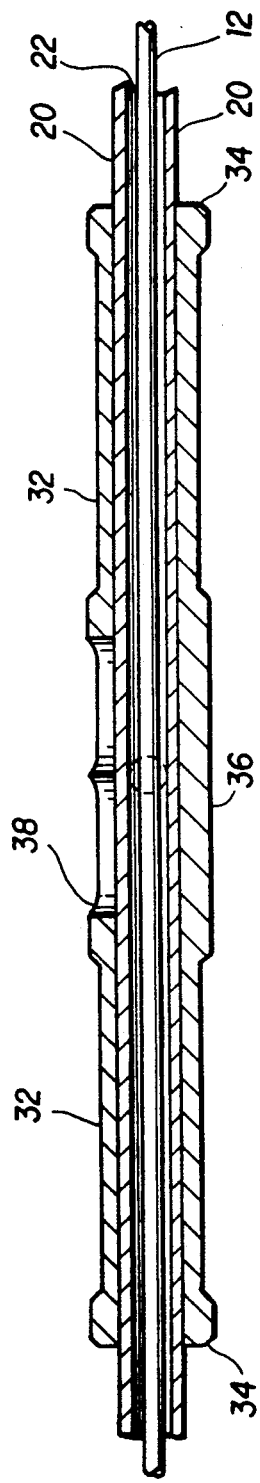
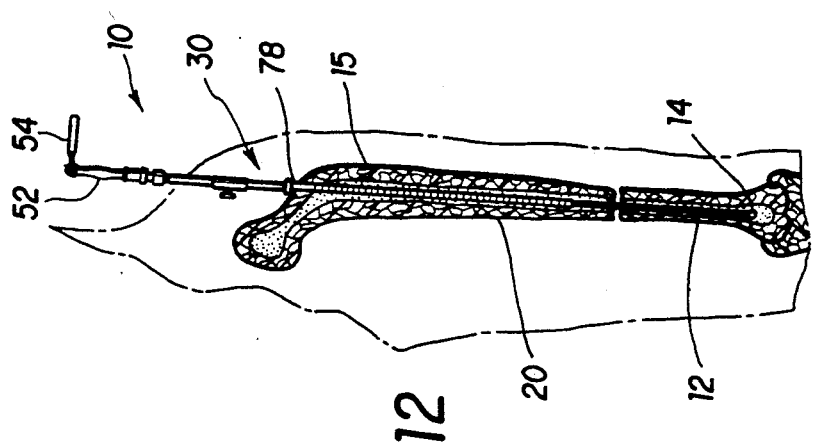
FIG. 11
FIG. 12

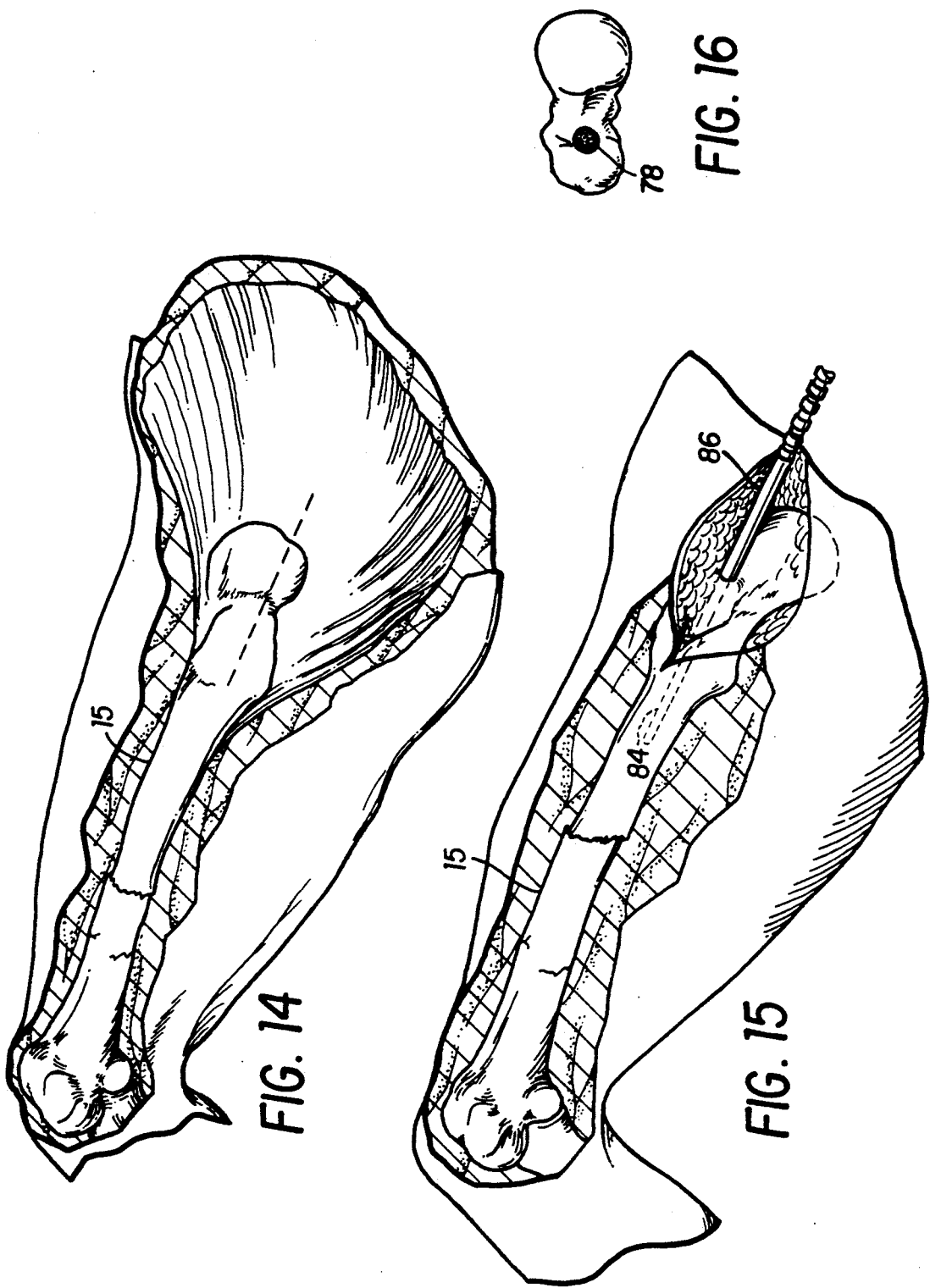

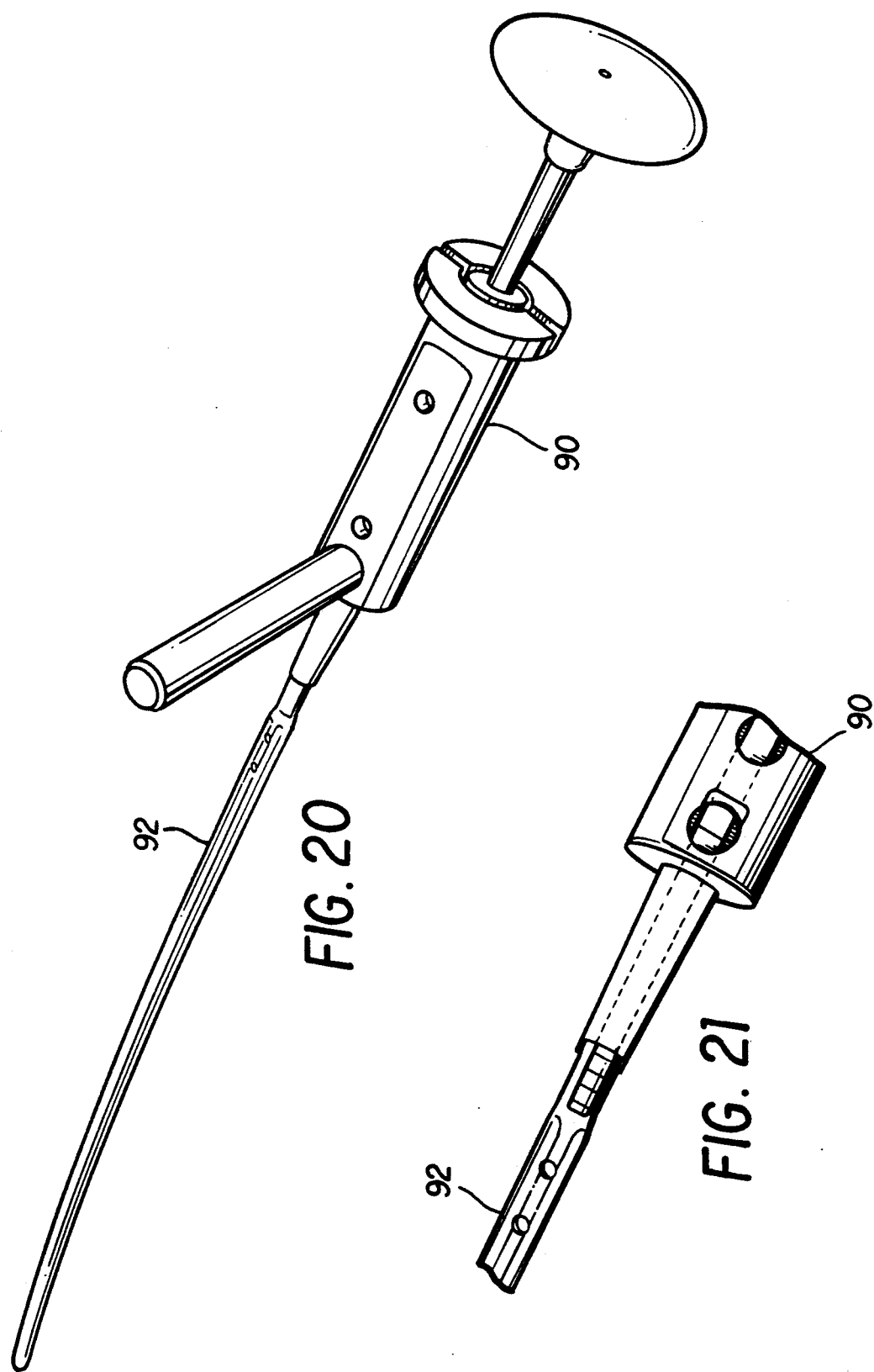

APPARATUS FOR REDUCING A FRACTURE

FIELD OF THE INVENTION

The present invention generally relates to an apparatus for reducing the fracture of a bone and, in particular, to a tool for reducing the fracture of a femur.

BACKGROUND OF THE INVENTION

In the field of orthopedics, various techniques are employed for holding together parts of a fractured bone during the healing process. However, prior to the fixation of the bone fragments, it is first required that the fracture be reduced, that is, the various bone fragments or pieces must be repositioned in their proper relative arrangement before the fractured bone can be fixed or stabilized for healing. U.S. Pat. No. 4,103,683 generally refers to reduction of a fracture which is maintained with suitable bone clamps.

Another reduction technique is illustrated and described in U.S. Pat. No. 4,127,119 which includes upper and lower pin holder assemblies that have a ring-like configuration and can be positioned about the limb to be reduced. Bone penetrating pins are secured to the appropriate pin holders in these assemblies. A solely external fracture reduction system is described in U.S. Pat. No. 3,850,166. However the apparatus of this '166 patent is intended for use only for lower limb fractures. Moreover, it is not suitable for complicated fractures which result in disorientation of the bone fragments.

Still yet another fracture reduction apparatus is described in U.S. Pat. No. 4,628,922 which illustrates single-sided fixation of a bone fracture which requires fixation pins to be inserted through the bone fragments. Although this device is said to be able to reduce the fracture, it involves a relatively complicated procedure in that movement of one component will affect the orientation of any other component. Furthermore, rotation is limited in view of the skin and tissue through which the pins penetrate.

The use of elastic nails is described in U.S. Pat. No. 4,467,983. In the example illustrated, the nails are passed into the medullary canal through a hole in the bone and can be rotated so as to reduce the fractured femoral head. However, these nails at the least are not convenient for measurement of the final nail to be inserted for fixation of the fracture. Furthermore, these nails require special configurations as well as elastic portions, as noted, in order to permit their use in the reduction process. Since the bone hole serves as a fulcrum point, these nails are not capable of fine adjustment or ease of use within the medullary canal.

We have invented a tool for reducing fractures and particularly for reduction of a fractured femur which overcomes the limitations noted above. The fracture reduction tool of the present invention is useful in reducing the fracture, in passing the reaming guide wire and in measuring the length of the nail or rod to be using in ultimately fixating the fracture. These procedures are not collectively available with any of the aforementioned prior art devices. Moreover, the tool of the present invention can also be used for different lengths of bone and accordingly avoids the need for tools of various sizes.

SUMMARY OF THE INVENTION

The present invention is directed to an apparatus for reducing a fractured bone, comprising shaft means configured and dimensioned for passage of its distal end into the medullary canal of the fractured bone through a suitably sized aperture for manipulating into and within the medullary canal by translational and/or rotational movements so as to reduce the fractured bone, the shaft means having a first bore along its length, and measurement means configured and dimensioned for movement over at least a portion of the shaft means, so as to permit determination of the length of a nail to be inserted into the medullary canal of the reduced bone.

According to one preferred embodiment, the shaft means is a hollow elongated shaft of a generally uniform diameter along its length and is beveled at its distal end. Also the first bore of the shaft is of a generally uniform diameter along its length. The shaft preferably has unevenly spaced apart graduations along a portion thereof. These graduations which cooperate with the measurement means for determination of the nail length and are in the range of thirty through forty-eight centimeters with one centimeter increments.

The measurement means comprises a tubular sleeve movable at least along the portion of the shaft having the graduations. The tubular sleeve includes a window so as to permit viewing of the graduations on the shaft under the window. An arrow indicator is positioned generally midway of the window so as to aid in measurement of the length of the nail to be inserted. Means are provided for selectively locking the measurement means in a predetermined position on the shaft. The tubular sleeve further comprises a passageway communicating with the outer surface of the shaft. The measurement locking means comprises a screw dimensioned and configured for cooperative engagement with the passageway so that the screw can be advanced into the passageway and thereupon contact the outer surface so as to selectively lock the tubular sleeve in position on the shaft.

The apparatus of the present invention further comprises handle means coupled to the proximal end of the shaft for aid in manipulating the shaft into and within the medullary canal, the handle means having a second bore along its length aligned coaxially with the first bore of the shaft. This handle means comprises an elongated handle body which is open at one end to receive the proximal end of the shaft therein. Chuck means are provided for selectively securing the shaft to the handle body. The chuck means comprises first threads positioned adjacent the open end of the handle body and a collar having a bore dimensioned and configured so as to permit movement of the collar along at least the proximal end of the shaft. The collar has second threads within its bore corresponding to the first threads on the handle body so as to permit cooperative engagement of the first and the second threads such that the open end of the handle body is selectively pressed by the collar into contact with the shaft for securement thereof. The handle means further comprises a generally tubular handle grip positioned about a portion of the elongated handle body. The handle means further comprises a handle rod positioned on the distal end of the handle body and extending transversely to the second bore.

In a preferred embodiment, the apparatus for use with a guide wire for reducing a fractured bone. The first bore of the shaft means has a diameter greater than the general diameter of the guide wire to allow selective passage of the guide wire through the first bore. Means are also provided for selectively locking the guide wire within the second bore in a predetermined position relative to the shaft means.

According to another preferred embodiment, the present invention is directed to an apparatus for use with a guide wire for reducing a fractured femur, the guide wire being of a generally uniform diameter and having an enlarged distal end portion for placement into the medullary canal of the fractured femur, comprising shaft means configured and dimensioned for passage of its distal end into the medullary canal of the fractured femur through a suitably sized aperture to accommodate passage of the shaft means into the medullary canal and for manipulating at least either the shaft means or the guide wire into and within the respective medullary canal portions of the fractured femur by translational and/or rotational movements so as to reduce the fractured femur, the shaft means having a first bore along its length, the first bore having a diameter greater than the diameter of the guide wire to allow selective passage of the guide wire through the first bore, and measurement means configured and dimensioned for movement over at least a portion of the shaft means, so as to permit determination of the length of a nail to be inserted into the medullary canal of the reduced bone.

The apparatus further comprises handle means coupled to the proximal end of the shaft for aid in manipulating the shaft into and within the medullary canal. The handle means has a second bore along its length aligned coaxially with the first bore of the shaft. This second bore has a diameter greater than the diameter of the guide wire to allow selective passage of the guide wire through the second bore.

Preferably, the handle grip is integrally molded about the portion of the elongated handle body. The apparatus further comprises means for selectively locking the guide wire within the second bore in a predetermined position relative to the shaft means. The handle body comprises a passageway communicating with and extending transversely to the second bore. The guide wire locking means comprises a rod dimensioned for positioning in the handle body passageway and extending therefrom to a free end. The rod has a cam positioned thereon so that the cam enters into the second bore during at least a portion of one complete rotation of the rod. The cam is configured and dimensioned so that the cam when entering the bore will contact and selectively lock the guide wire within the second bore in position relative to the shaft. A knob is secured to the free end of the cam rod for ease in rotating the cam rod.

The present invention is also directed to a method for reducing a fractured bone such a femur, whereby a portion of the fractured bone is exposed as an entry site in medullary canal of the fractured bone. At the entry site an entry hole is drilled into the medullary canal. A fracture reducing apparatus is inserted with a guide wire therein through the entry hole into the medullary canal. At least one of either the shaft means or the guide wire is manipulated through the medullary canals of the fragment portions of the fractured bone so as to reduce the fracture.

The method further comprises providing measurement means on the shaft means prior to insertion through the entry hole, the measurement means configured and dimensioned for movement over at least a portion of the shaft means, so as to permit determination of the length of a nail to be inserted into the medullary canal of the reduced bone, advancing the distal end of the guide wire generally into contact with the distal end of the medullary canal, positioning the fracture reducing apparatus so that its proximal end is flush with the proximal end of the guide wire, positioning the measurement means so as to abut the exposed portion of the fractured bone, and determining from the measurement means the length of the nail or rod to be inserted through the medullary canal.

BRIEF DESCRIPTION OF THE DRAWINGS

The present invention is described in detail below with reference to the drawings wherein:

FIG. 2 is a side view of the fracture reducing tool of FIG. 1 in assembled form together with a guide wire positioned through the shaft and handle body.

FIG. 3 is a partial cross-sectional side view of the tool as shown in FIG. 1 taken along the lines 3—3 of FIG. 2.

FIG. 4 is a cross-sectional view of the tool as shown in FIG. 1 taken along the lines 4—4 of FIG. 2.

FIG. 5 is a cross-sectional view of the handle body and guide wire taken along the lines 5—5 of FIG. 2 and an exposed view of the cam knob in the unlocked configuration.

FIG. 6 is a cross-sectional view taken along the lines 6—6 of FIG. 5 illustrating rotation of the cam knob to lock the guide wire within the shaft.

FIG. 7 is a cross-sectional view taken along the lines 7—7 of FIG. 5.

FIG. 8 is a cross-sectional view taken along the lines 8—8 of FIG. 2.

FIG. 9 is a cross-sectional view taken along the lines 9—9 of FIG. 8.

FIG. 10 is a cross-sectional view taken along the lines 10—10 of FIG. 2 illustrating the thumb screw locking the measuring sleeve on the shaft.

FIG. 11 is a cross-sectional view of the shaft and measuring sleeve taken along lines 11—11 of FIG. 2 and an exposed view of the guide wire within the shaft.

FIG. 12 is a partially cross-sectional view of a human femur with the tool of the present invention and a guide wire positioned within the medullary canal of the femur.

FIG. 14 illustrates exposure of the greater trochanter.

FIG. 15 illustrates enlargement of the entry hole for the tool of the present invention.

FIG. 16 is an end view of the proximal end of the femur with the enlarged entry hole.

FIG. 20 illustrates a rod driver mounted onto a rod.

FIG. 21 illustrates the secure fastening of the self-locking threading bolt and the T-handle wrench onto the rod.

FIGS. 26 and 26A illustrate positioning of the serrated-end guide sleeve through the guide and down through to the lateral cortex.

DETAILED DESCRIPTION OF THE INVENTION

In the description which follows, any reference to either direction or orientation is intended primarily and solely for purposes of illustration and is not intended in any way as a limitation of the scope of the present invention. Also, the particular embodiments described herein, although being preferred, are not to be considered as limiting of the present invention. Furthermore, like parts or elements in the various drawings hereto are identified by like numerals for ease of reference.

Figure 1:
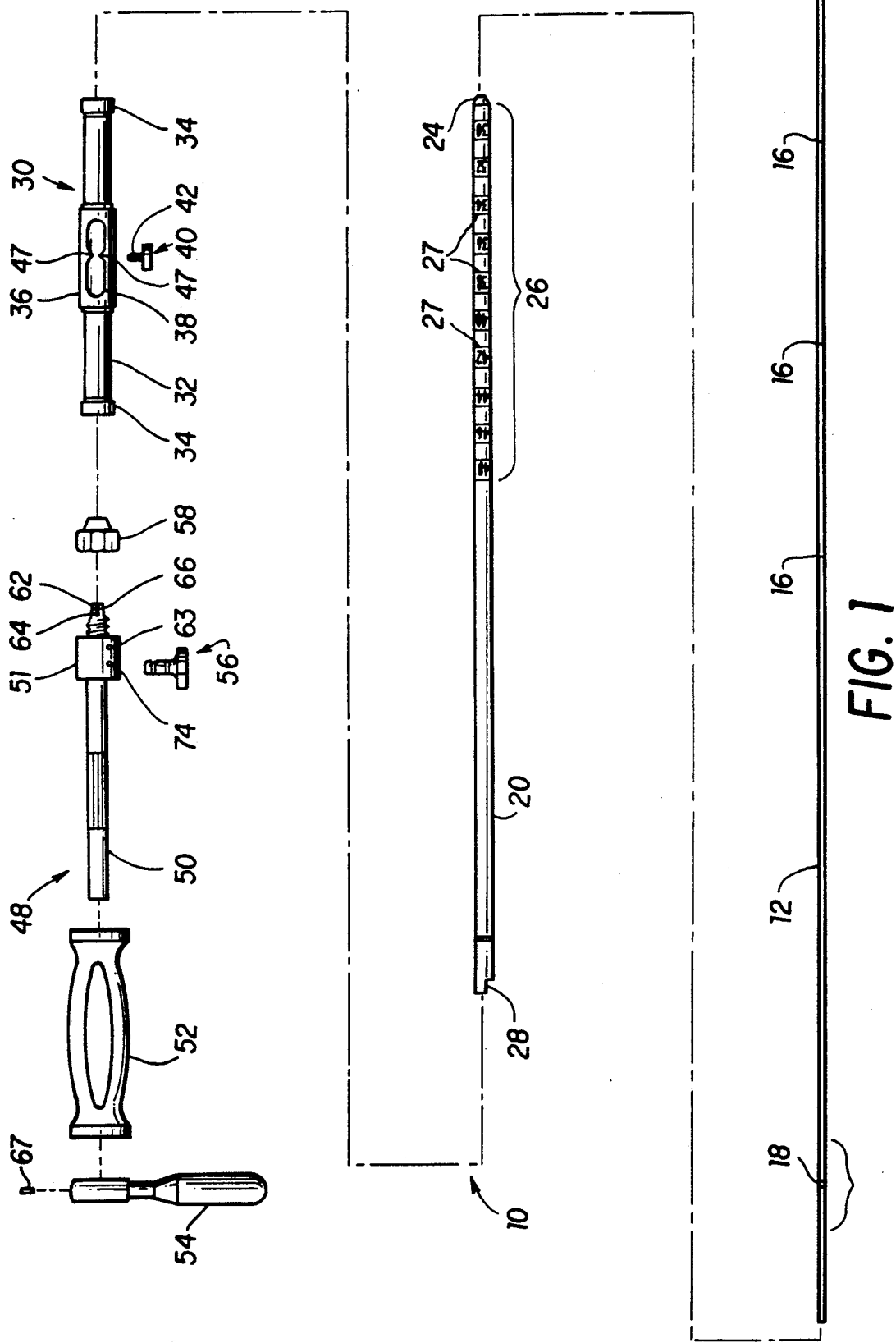
FIG. 1 is an exploded view of a tool for reducing a fracture of a bone according to the present invention illustrating separately a shaft, measuring sleeve with thumb screw, collar, handle body, cam knob, handle and handle arm, together with a guide wire.

A fracture reduction tool 10 according to the present invention is shown in FIG. 1 in exploded form to illustrate the various components involved in its assembly. Also shown is a guide wire 12 which has an overall length greater than the length of the tool 10 when assembled. Guide wire 12 is of a typical straight construction and configuration and has a uniform diameter with an enlarged or beaded distal end 14 which is inserted into the medullary canal of the fractured bone such as a femur 15 as shown in FIG. 12. The guide wire 12 is inscribed at the distal portion with length marks 16 which typically are ten centimeters apart and at the proximal portion with an overall length marking 18.

As shown in FIG. 1, the tool 10 is formed of an elongated hollow shaft 20 which has a bore 22 shown more clearly in FIG. 11 for passage of guide wire 12. Accordingly bore 22 has a uniform diameter which is at least slightly larger than the diameter of guide wire 12 unrestricted passage therethrough. The distal end 24 of shaft 20 is beveled which aids in the penetration of the shaft 20 through the marrow within the medullary canal of the femur 15 as shown in FIG. 12. The distal portion 26 of shaft 20 also has inscribed thereon a plurality of length markings or graduations 27. Preferably these graduations 27 are shown in one centimeter increments. In the preferred embodiment, the range of these increments extends from about thirty centimeters to forty-eight centimeters which provides for use of this tool 10 with a variety of different sized bones and, in particular, the femur of the human body. At its proximal end, the shaft 20 has a notch 28 as shown in FIG. 1 which is helpful in the assembly of tool 10 as explained more fully below.

Although as described herein, the fracture reducing tool 10 of the present invention is preferred for use in reducing fractures of the femur, it is contemplated that such tool 10 can also be used with other fractured bones with proper sizing of the shaft 20 so as to permit its entry and passage within the medullary canal of the respective fractured bone. Moreover, although the shaft 20 as shown in the preferred embodiments herein in the FIGS. is generally of a linear configuration, the shaft 20 can also be curved if desired in order to accommodate or correspond to the general curvature of the respective medullary canal involved.

Figures 18, 19:
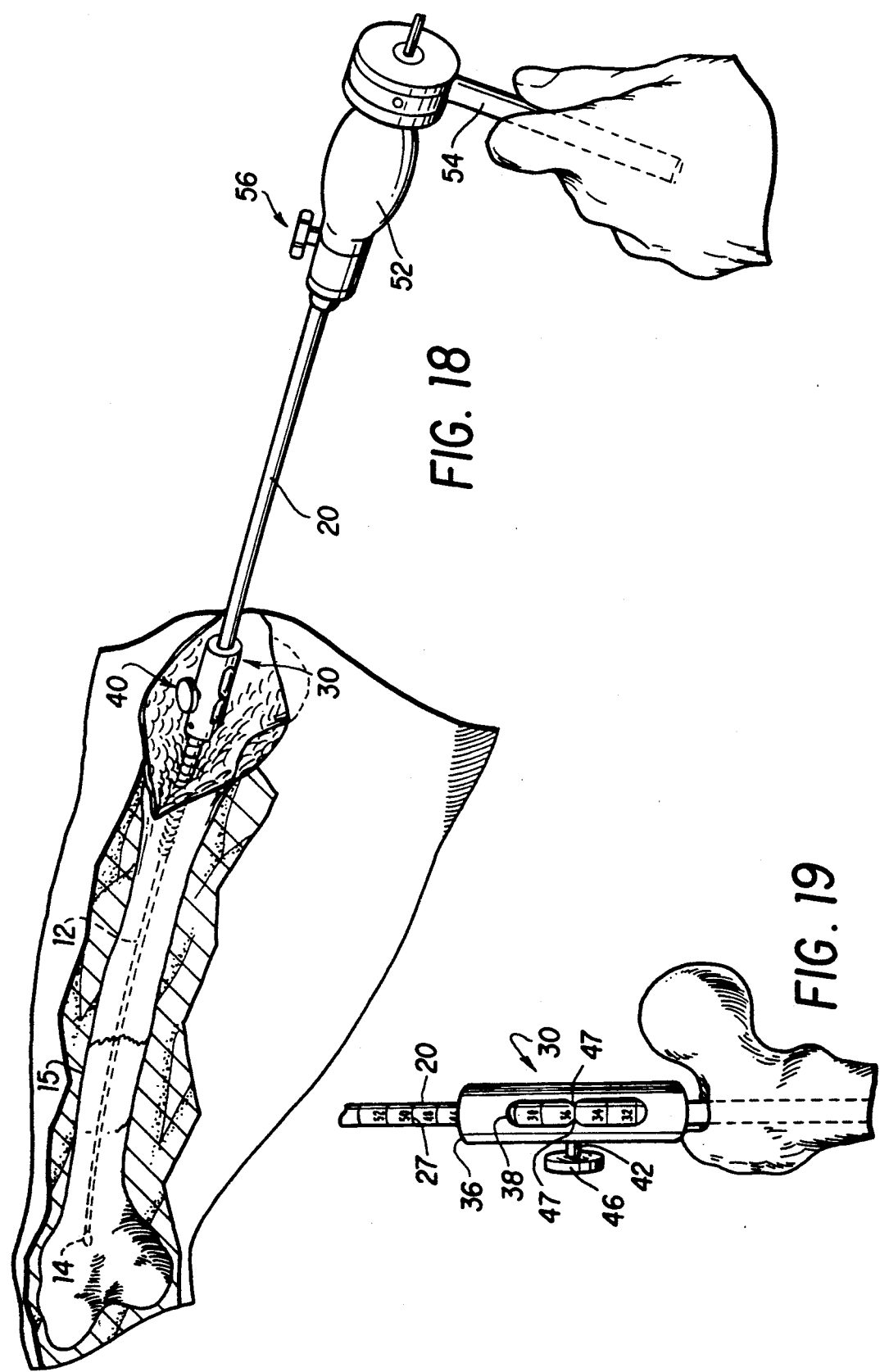
FIG. 18 illustrates the positioning of the measuring sleeve so as to abut the tip of the greater trochanter.
FIG. 19 illustrates the window and indicator arrow of the measuring sleeve in position over the graduations of the shaft so as to permit measurement of the rod or nail to be inserted into the medullary canal.

The tool 10 also includes a measurement member 30 which is a formed of tubular sleeve 32 having flange ends 34 and a body portion 36 with an oval window 38. The measurement sleeve 30 is sized in diameter so as to be capable of moving along and over the shaft 20 in the configuration as illustrated in FIG. 11. Sleeve 30 also includes a thumb set screw 40 which has a screw rod 42 as shown in FIG. 10 that is sized for threaded passage through passageway 44 in body portion 36. Screw rod 42 thus can be threaded against the outer surface of shaft 20. In this fashion, the measurement sleeve 30 can be selectively locked into position at a predetermined location of shaft 20 to allow for ease of measurement. The thumb set screw 40 includes a knurled disc 46 attached to the free end of screw rod 42 to allow for easy rotation of the thumb set screw 40. In operation, as the tubular sleeve 32 moves over the distal portion 26 of shaft 20, the graduations 27 are viewable through window 38 as shown in FIG. 19. Preferably the body portion 36 has opposed arrow indicators 47 as shown in FIGS. 1 and 19 which are positioned midway of the window 38 so as to aid in determining or measuring the length of the nail or rod to be inserted into the medullary canal for fixation.

The tool 10, as further shown in FIGS. 1 and 2, also includes a handle 48 which is formed of a cylindrical handle body 50 having an enlarged butt portion 51, handle grip 52 and handle rod 54. A cam rod 56 coupled to butt portion 51 allows for locking of the guide wire 12 selectively in position relative to the shaft 20 and handle 48. As shown in FIG. 3, the handle body 50 has a bore 60 along its length and through which the guide wire 12 can freely pass. A collar 58 by means of threads within its bore at a proximal portion can be threaded onto corresponding threads positioned as shown in FIG. 3 on the distal end of handle body 50. The distal end of handle body 50 also includes an open end 62 into which the shaft 20 can be inserted for coupling with the handle 48. This open end 62 is configured to receive the notch 28 which is tightly fitted therein by means of wedge pin 63 as shown in FIGS. 1, 2 and 9. Wedge pin 63 is flush mounted in butt portion 51, i.e., it is shaved or ground off after insertion so as to be flush with the outer surface of butt portion 51. Similarly, the handle rod 54 is secured onto handle body 50 by means of wedge pin 67. This pin 67 as shown in FIG. 3, is flush mounted with the outer surface of handle rod 54 and is preferably press-fitted through suitable holes in handle rod 54 and handle body 50.

The open end 62 also includes a series of cutaway portions 64 which leave fingers 66 as shown in FIG. 1 which together with collar 58 function as a chuck for securing or locking the shaft 20 together with the handle 48. As the collar 58 is screwed onto the open end 62, the cut-away portions 64 allow the fingers 66 to press into engaging contact with the outer surface of shaft 20 as shown in FIG. 3. In this fashion the collar 58 tightens down the fingers 66 so as to securely retain the shaft 20 within the open end 62 of handle 48. The bore 60 within the body handle 50 upon assembly is aligned coaxially with the bore 22 of shaft 20 as shown in FIG. 3. This permits guide wire 12 to be freely and selectively passed throughout the length of tool 10 until such time as it is locked in position by means of cam knob 56.

Referring to FIG. 5, the cam knob 56 includes a cam rod 68 which is positioned in a passageway in the butt portion 51 and extends therefrom to a free end. A four prong knob 70 is attached to the cam rod 68 free end. The cam rod 68 has a groove 72 which is suitably sized to receive a wedge pin 74 as shown in FIGS. 1, 2 and 7 which is flush mounted similar to wedge pin 63 and press-fitted through a hole in butt portion 51. Thus, the cam rod 68 can be rotated while kept in position within the respective passageway of butt portion 51. The cam rod 68 also has a cam groove 76 whose outer surface acts as a cam as shown in FIG. 6 so that as the cam rotates, for example in the direction of the arrow, a greater portion of the cam enters the bore 60 during at least a portion of one complete rotation the cam rod 68. In this fashion, the cam groove 76 will contact the guide wire 20 and push it against and into contact with the opposing surface of bore 60 so as to selectively lock the guide wire 12 within the bore 60 in position relative to the butt portion 51 and shaft 20. This operation is demonstrated in FIG. 6 wherein the guide wire 12 shown in solid form is advance toward its position shown in phantom lines.

As noted, the guide wire 12 with its beaded end 14 is assembled with tool 10 by insertion through bores 22 and 60 in the manner shown in FIG. 2. Thereafter, the tool 10 and guide wire 12 can be inserted through a suitably sized entry hole 78 shown in FIG. 16, and into the medullary canal of femur 15 as shown in FIG. 12. The tool 10 can then be positioned as desired within the medullary canal and the guide wire 12 extended through the canal portions so as to manipulate the various fragments of fractured femur 15. Once reduction is achieved, the guide wire 12 is fully inserted so that the beaded end 14 abuts the distal end of the medullary canal. The tool 10 can be positioned so that the proximal end of handle arm 54 is flush with the proximal end of guide wire 12. In this configuration, the measurement sleeve 30 is positioned so as to abut the greater trochanter of femur 15 as shown in FIG. 19. The arrow indicators 47 then provide a measurement of the pin or nail to be inserted into the medullary canal for fixation. Accordingly, the graduations 27 are calibrated to provide the nail or rod measurement when the tool 10 and guide wire 12 are positioned as described above. Although the tool 10 is preferably utilized with the guide wire 12 for reduction, alternatively the shaft 20 can be inserted as far into the medullary canal as desired so that reduction of the fragment portions can be achieved with shaft 20 itself.

With respect to the tool 10, its use in intramedullary (i.m.) rod surgical technique for a positioning and fracture reduction will now be discussed.

Figure 13:
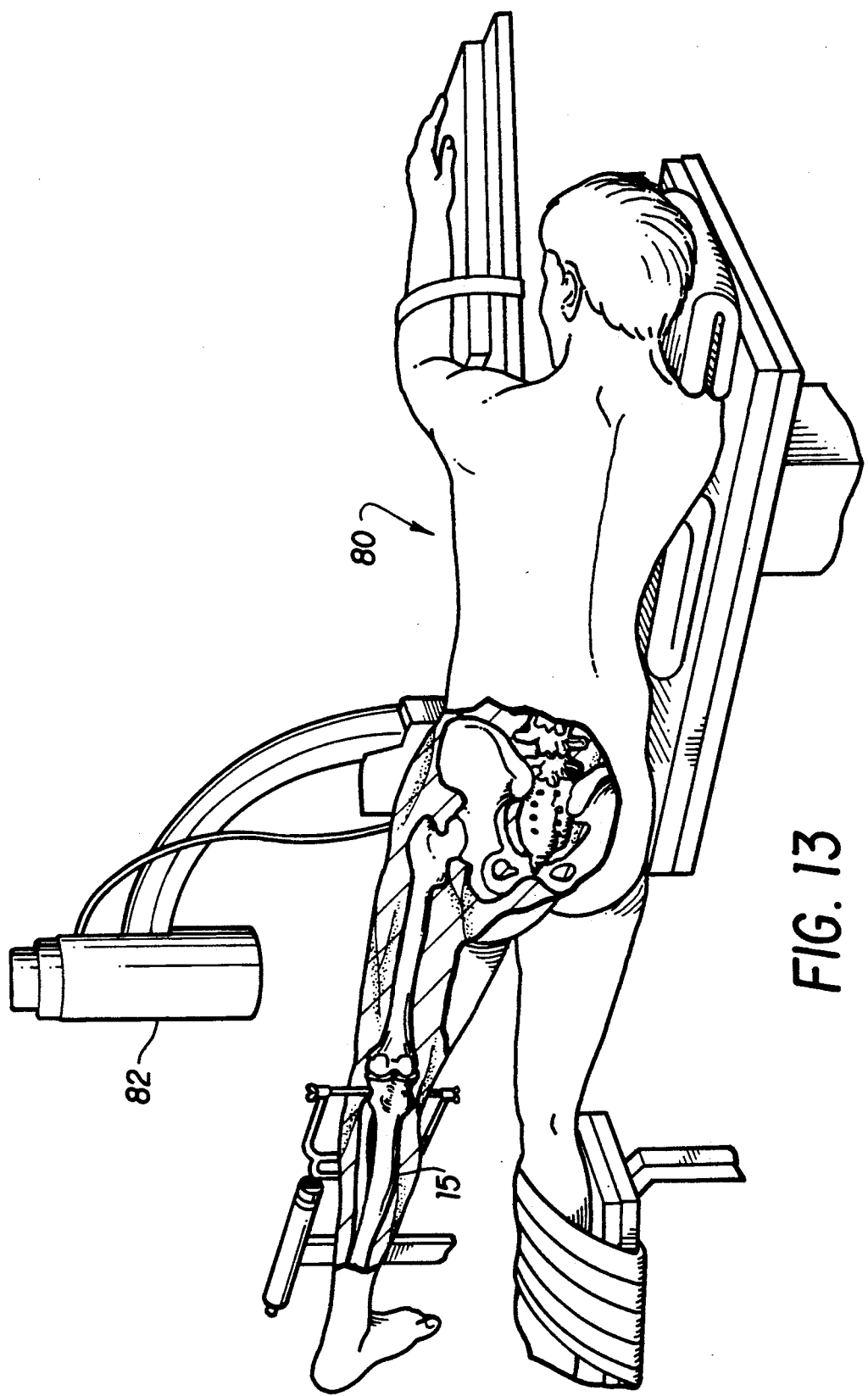
FIG. 13 illustrates a patient with a fractured femur resting in position on a fracture table.

Place the patient 80 on the fracture table in the lateral decubitus position as shown in FIG. 13. The supine position may also be used. Reduce the fracture in your usual manner. With this technique, anatomical reduction of the fracture prior to insertion of the reduction tool 10 is not necessary. However, the fracture must be reducible. Confirm this with the C-arm fluoroscope 82, positioned to permit good anteroposterior and lateral views from the hip to the knee.

Perform standard surgical preparation and draping of the skin. If cross-locking is to be done, the surgeon must allow adequate clearance at the knee, as well as the hip. Make a 10-centimeter incision proximally from the tip of the greater trochanter in line with the fibers of the gluteus maximus. Expose the entry site as shown in FIG. 14.

The proper entry site for the nail is very important and must be located directly over the medullary canal. The entry point is the fossa on the underside of the greater trochanter at its junction with the femoral neck in the midline of the anteroposterior plane. Drill a 3.2 mm hip bolt guide pin 84 through the fossa into the medullary canal. Verify critical position of this pin in the canal with biplanar views on the fluoroscope 82.

Enlarge the entry hole 78 using the 14 mm hip bolt reamer 86 over the guide pin as shown in FIG. 15. Once this entry 78 illustrated in FIG. 16 has been made, remove the reamer 86 and guide pin 84.

The fracture reduction tool 10 is used to: reduce the fracture, help pass the reaming guide wire and measure the length of nail to be used. Load the 3.0 mm × 1000 mm bead-tip guide wire 12 into the reduction tool 10 by passing it retrorrade. Place the locking T-handle 88 on the proximal end of the wire 12.

Figure 17:
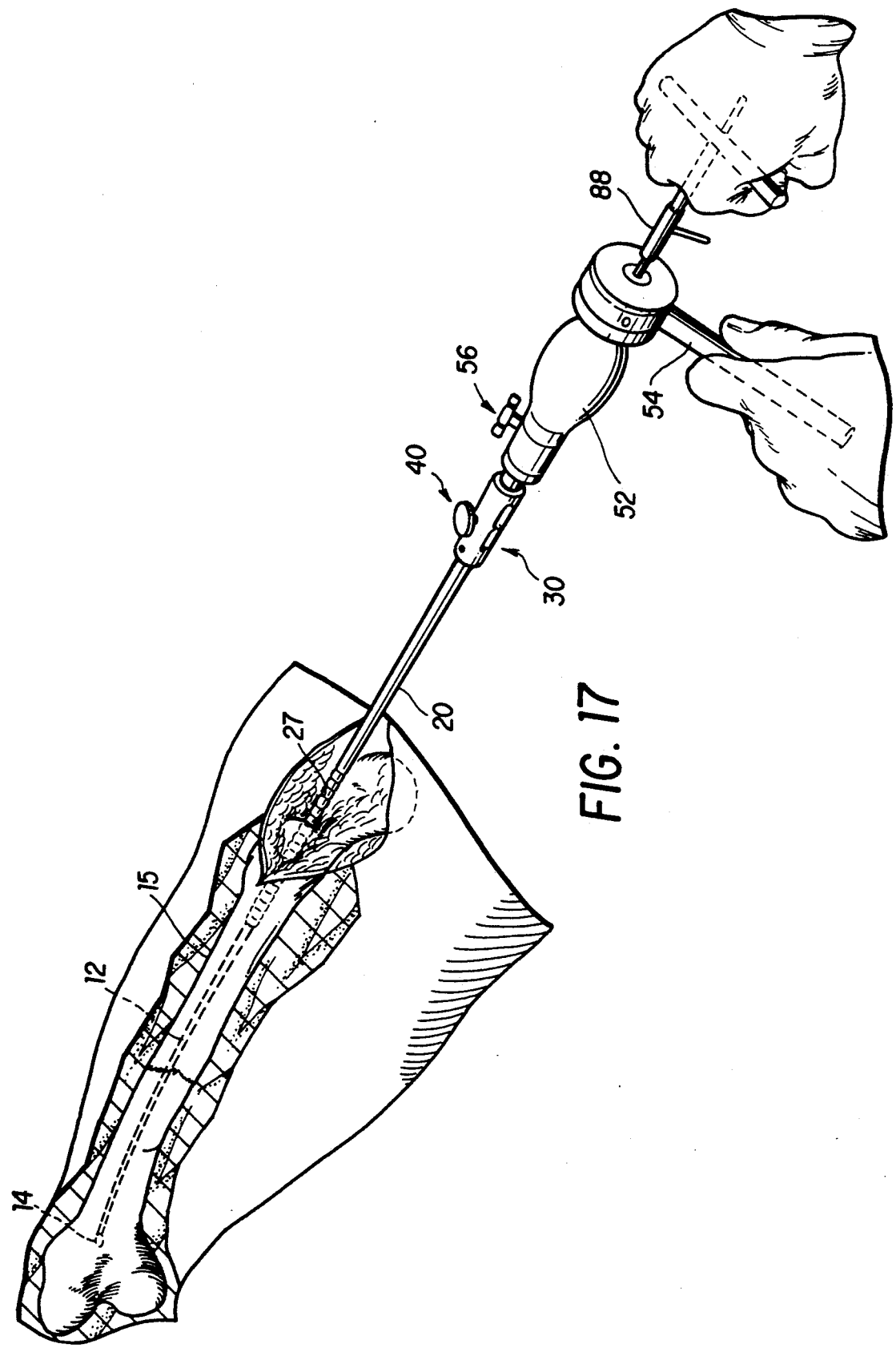
FIG. 17 illustrates the positioning of the tool together with a guide wire within the medullary canal of the fractured femur.

Insert the guide wire 12 and reduction tool 10 into the proximal fragment. Reduce the fracture using the fracture reduction tool 10 as a lever to manipulate the proximal fragment. Reduction is usually easy, except in supracondylar fractures, where flexion of the distal fragment may require an additional anteriorly directed push on the proximal end of the distal fragment by an assistant. Advance the guide wire using the T-handle 88 to manipulate the wire 12. If necessary, the reduction tool can be locked onto the wire 12 to drive it into the cancellous bone of the distal fragment. Verify proper position of the guide wire 12 with the fluoroscope 82 as shown in FIG. 17.

Remove the locking T-handle 88. Slide the reduction tool 10 until it is flush with the proximal end of the guide wire 12, and lock it in place with cam knob 56. Slide the measuring sleeve 30 down the tool 10 until it abuts the tip of the greater trochanter, and lock it in place with the thumbscrew 40 as shown in FIG. 18. Read the rod length from the reduction tool 10 scale 26 as illustrated in FIG. 19. Unlock and remove the reduction tool 10. Alternatively, the scale 26 can be read after the tool 10 is removed.

Ream the medullary canal progressively using flexible reamers. Begin with the smallest end-cutting reamer. In most cases, ream 1.5 mm larger than the rod to be used. When cross-locking, ream 2 mm larger if nondisplaced shaft fractures are suspected or when fixing distal third fractures. The superior strength of the Alta TM nail permits use of smaller diameter rods than previously recommended with other systems. As reamer sizes vary somewhat by manufacturer, the surgeon must check the size of reamers used.

Placement of the i.m. rod in the i.m. rod surgical technique will now be described.

Exchange the bead-tip 14 reaming guide wire 12 for a 3.2 mm × 1000 mm smooth-end guide wire, using the medullary tube to maintain fracture reduction.

Mount the rod driver 90 onto the proper size nail or rod 92 using the self-locking threaded bolt and the T- handle wrench as shown in FIGS. 20, 21. Be certain that the bolt is securely tightened.

The driving handle may be attached to control rotation as the nail or rod 92 is being driven.

Place the nail or rod driver 90 assembly over the guide wire and into the femoral entry site. Occasionally, some manipulation is required to pass the rod-driver junction locking over the end of the guide pin.

Figure 22:
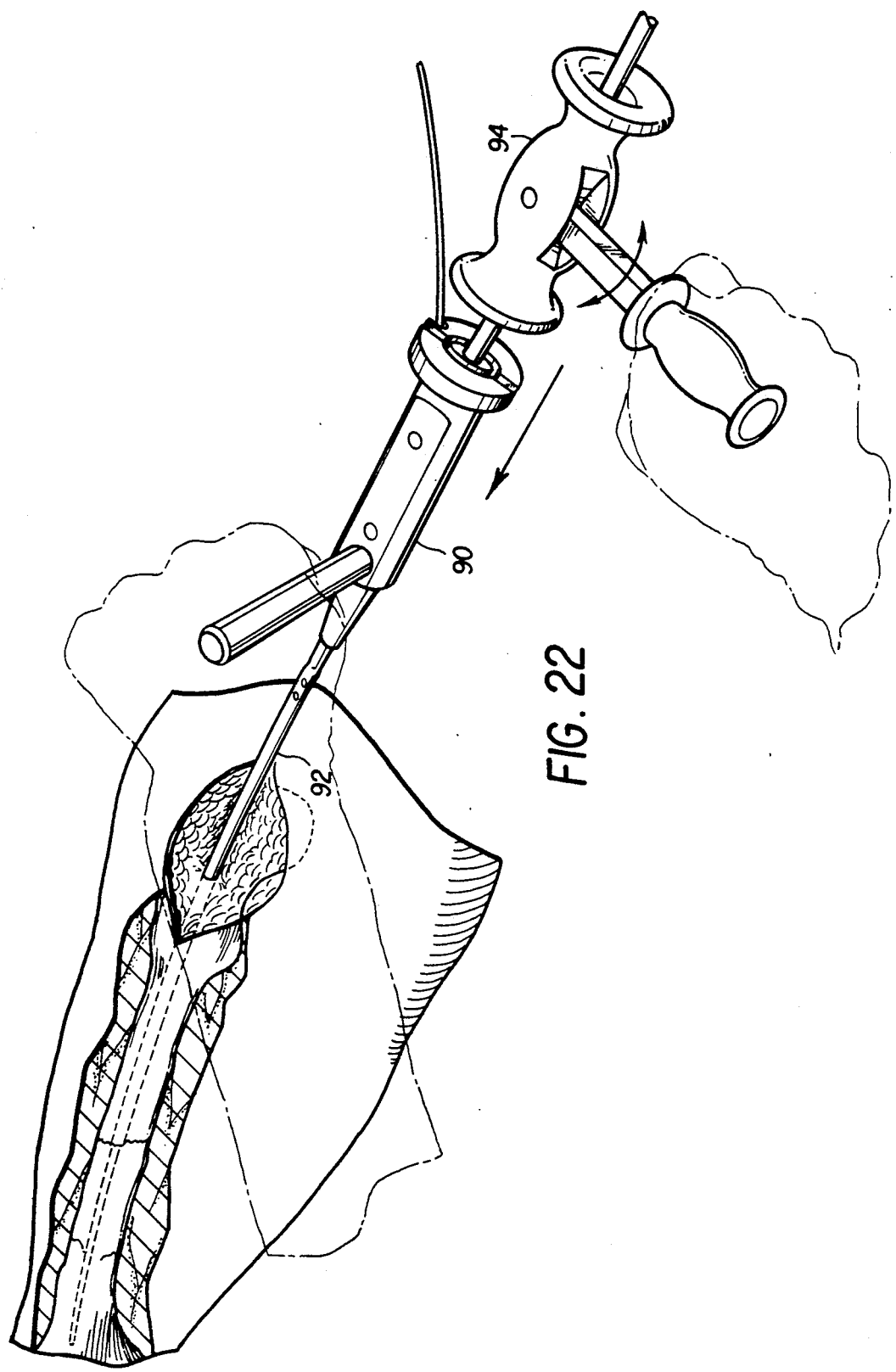
FIG. 22 illustrates driving the nail with the sliding hammer assembly.

With pilot point directed into the driver, attach the sliding hammer assembly 94 to the driving handle 90. Confirm proper rotation orientation of the rod. The guide wire must be deflected out the side of the driver assembly and be monitored to be certain that it does not advance with the nail. Drive the nail 92 with gentle blows. The nail 92 may also be driven with a mallet directly on the driving handle as shown in FIG. 22. Drive the nail 92 to the desired position. The rod 92 must progress smoothly without excessive force. If too much resistance is encountered, verify proper rod size and position. Additional reaming may be required. Drive the rod 92 until the proximal end is just above the level of the superior femoral neck.

Figure 23:
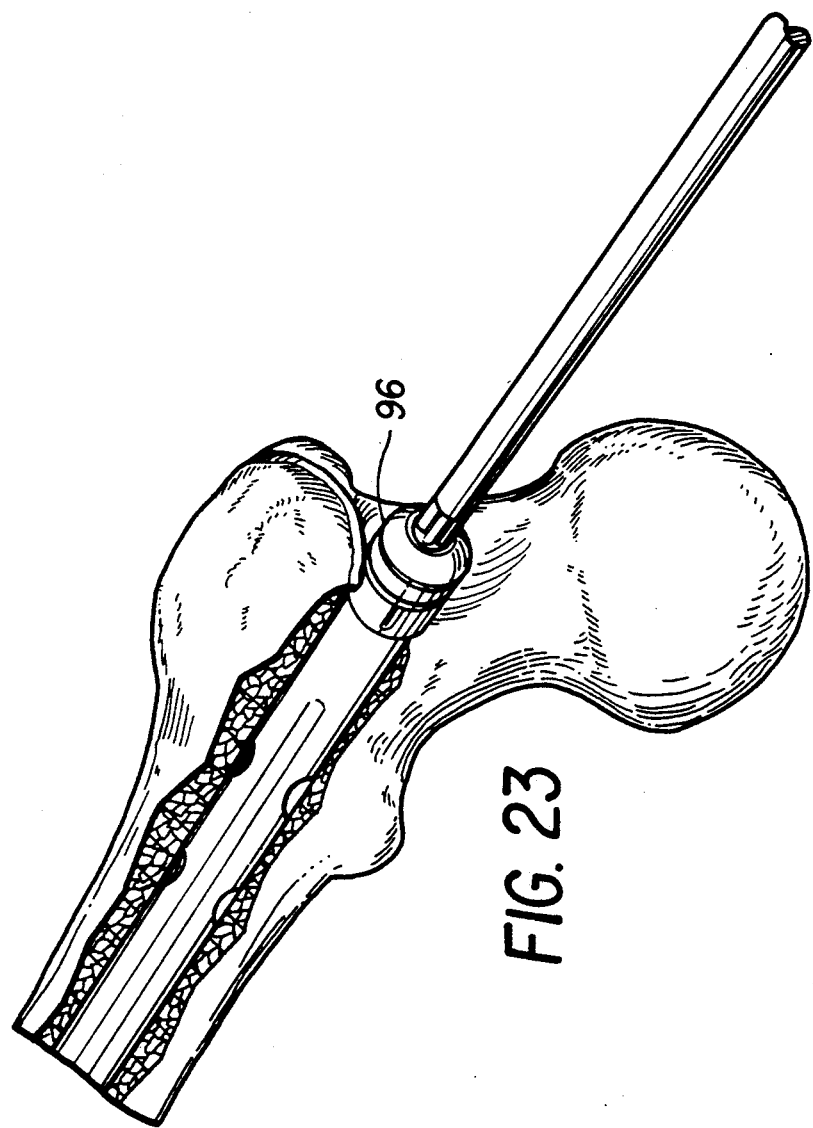
FIG. 23 illustrates insertion of the rod cap screw.

Remove the guide wire and the sliding hammer assembly 94. Then insert the rod cap screw 96, which facilitates removal of the rod by preventing bone ingrowth, using the T-40 Torx ® bit (FIG. 23). Note that the cap screw will appear on X-rays to be proud because of the radiolucent washer.

The cross-locking screw procedure for the i.m. rod surgical technique will now be presented.

Figure 24:
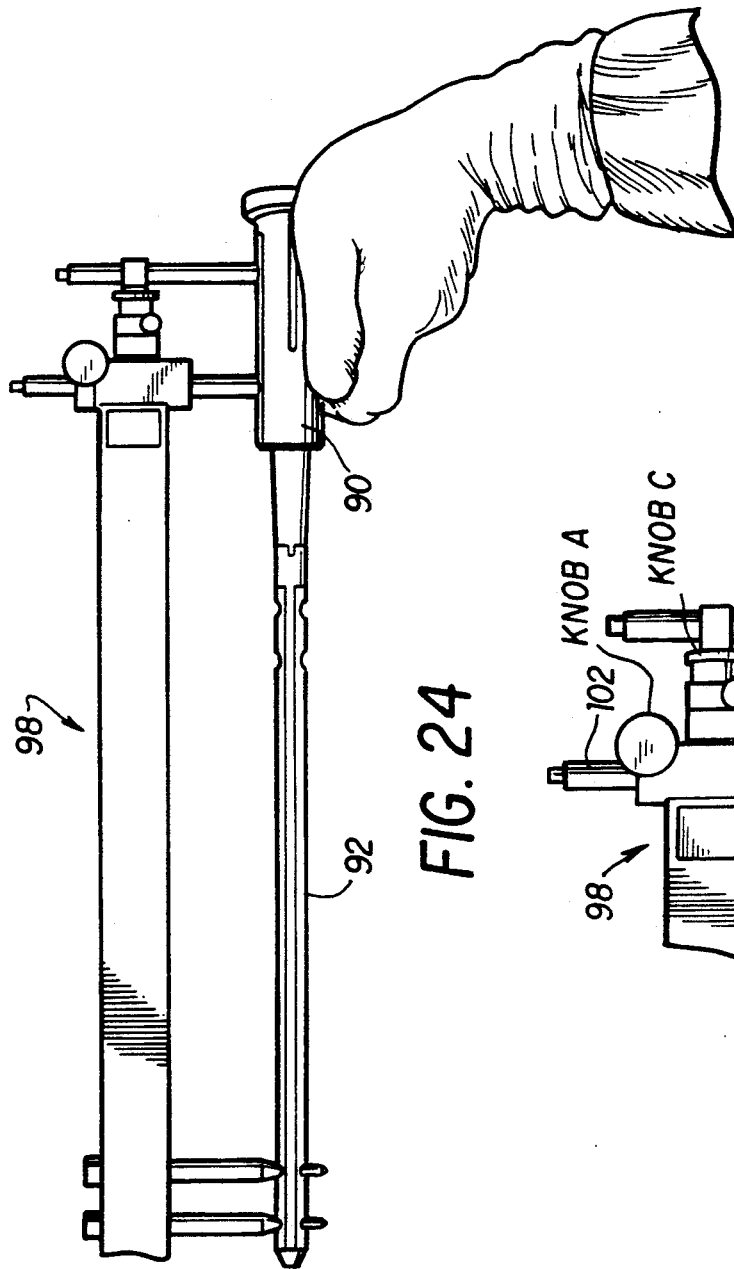
FIG. 24 illustrates a cross-locking drill guide.
Figure 25:
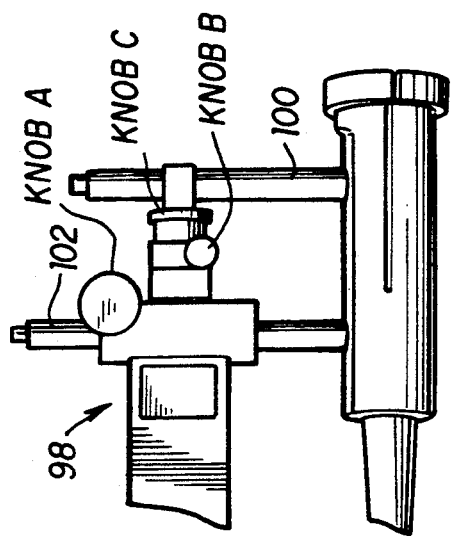
FIG. 25 illustrates the proximal end portion of the cross-locking drill guide of FIG. 24.

Prior to driving the rod 92, assemble the cross-locking drill guide 98 and set the cross-screw alignment. Mount the cross-locking drill guide 98 onto the driver assembly 90 as shown in FIG. 24. Note that the shorter 100 of the two mounting pins 100 and 102 is placed proximally. Slide the guide 98 over the mounting pins 100, 102. Estimate sufficient clearance to allow for the soft tissues of the thigh. Lock the guide 98 into place by hand-tightening Knob A as shown in FIG. 25. Place the two pilot pins in the distal guide holes on either side of the number representing the proper rod length.

Unlock Knob B, and adjust the guide 98 using the knurled adjustment wheel C until the pilot pins drop through the guide 98 into the center of the distal screw holes in the rod 92. During this procedure it is important to hold the rod 92 and cross-locking drill guide 98 only by the driving handle 90 as shown in FIGS. 24 and 25.

Lock the guide 98 into position by tightening Knob B with the T-wrench, then verify that alignment has been maintained. Remove the guide 98 by loosening the Knob A and sliding the guide 98 over the mounting pins 100, 102. Place the guide 98 gently on the sterile back table, being careful not to loosen Knob B. Drive the rod 92 as described hereinabove with respect to placement of the i.m. rod.

Remount the cross-locking drill guide 98 on the driving handle 90 as previously described. Be certain the guide 98 does not impinge on the patient 80 or any equipment.

Figure 26:
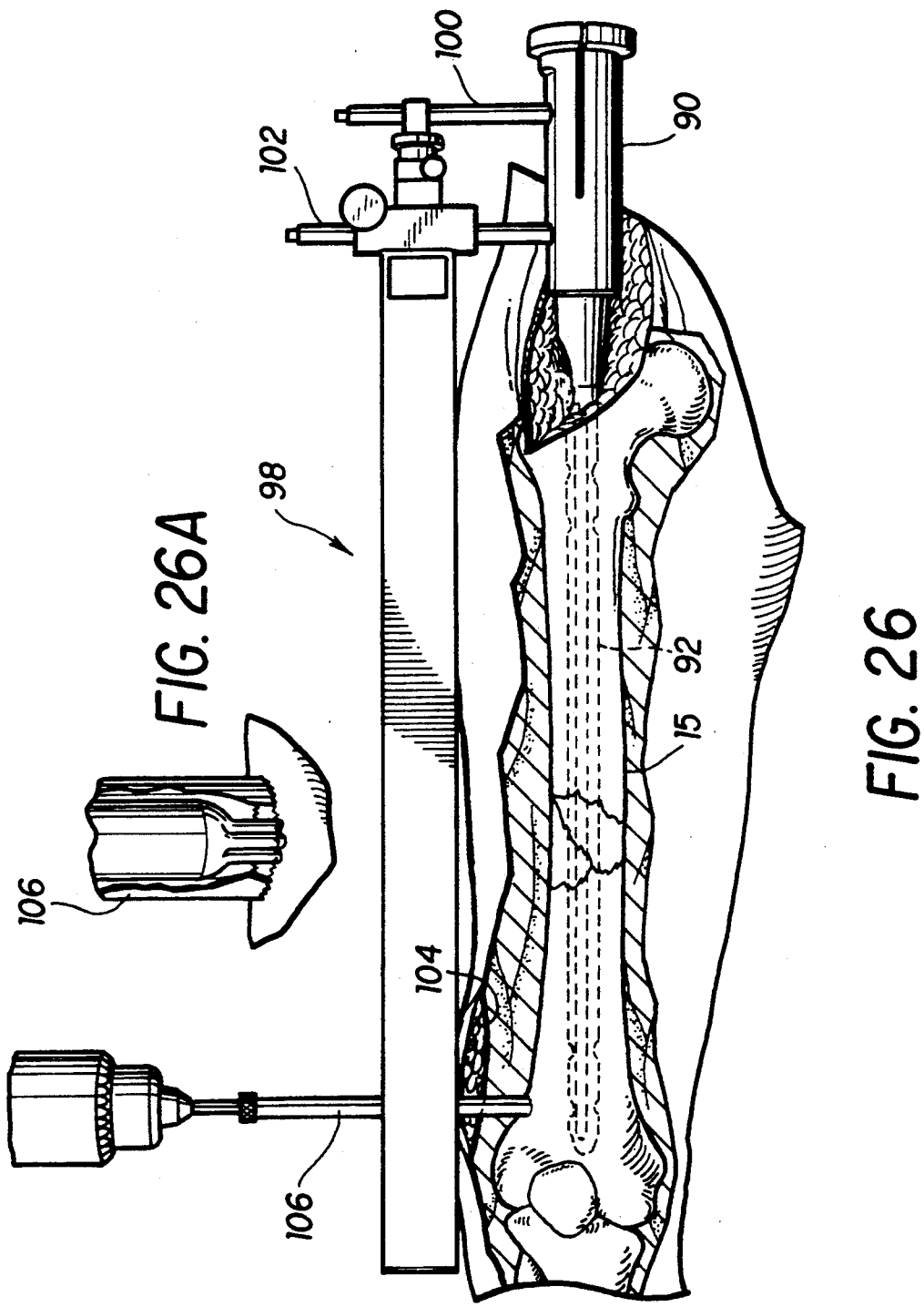

Distal cross-locking is performed first, except when only proximal cross-locking is required. This maximizes accuracy for the distal screws. Locate the incision site by placing two alignment pins through the appropriate guide holes and marking the skin. Make a single longitudinal incision 104 and expose enough lateral cortex of the femur 15 so that soft tissue impingement on the drill sleeves 106 does not occur as shown in FIG. 26.

Figure 27:
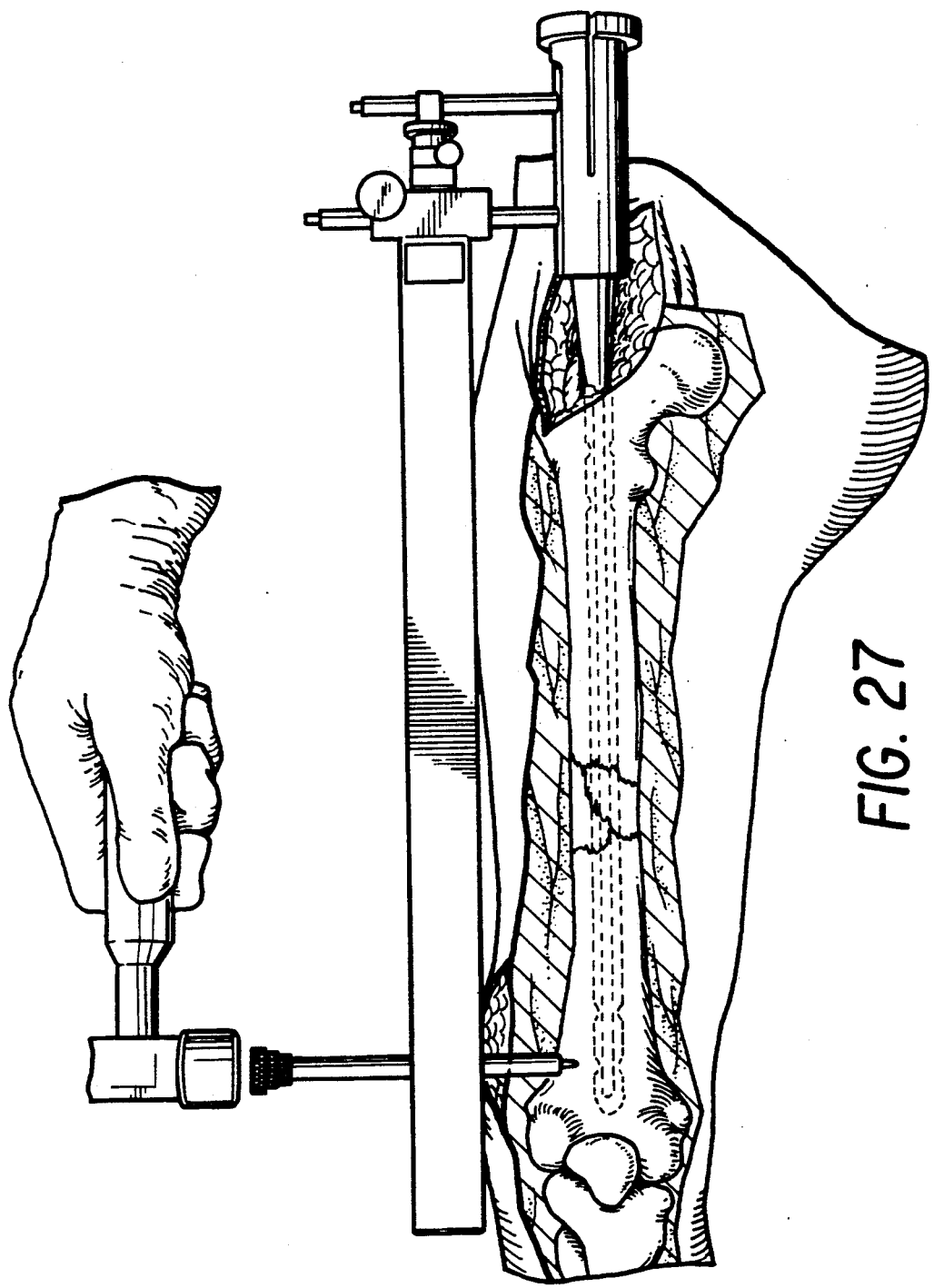
FIG. 27 illustrates marking a starting point for the drill.
Figure 28:
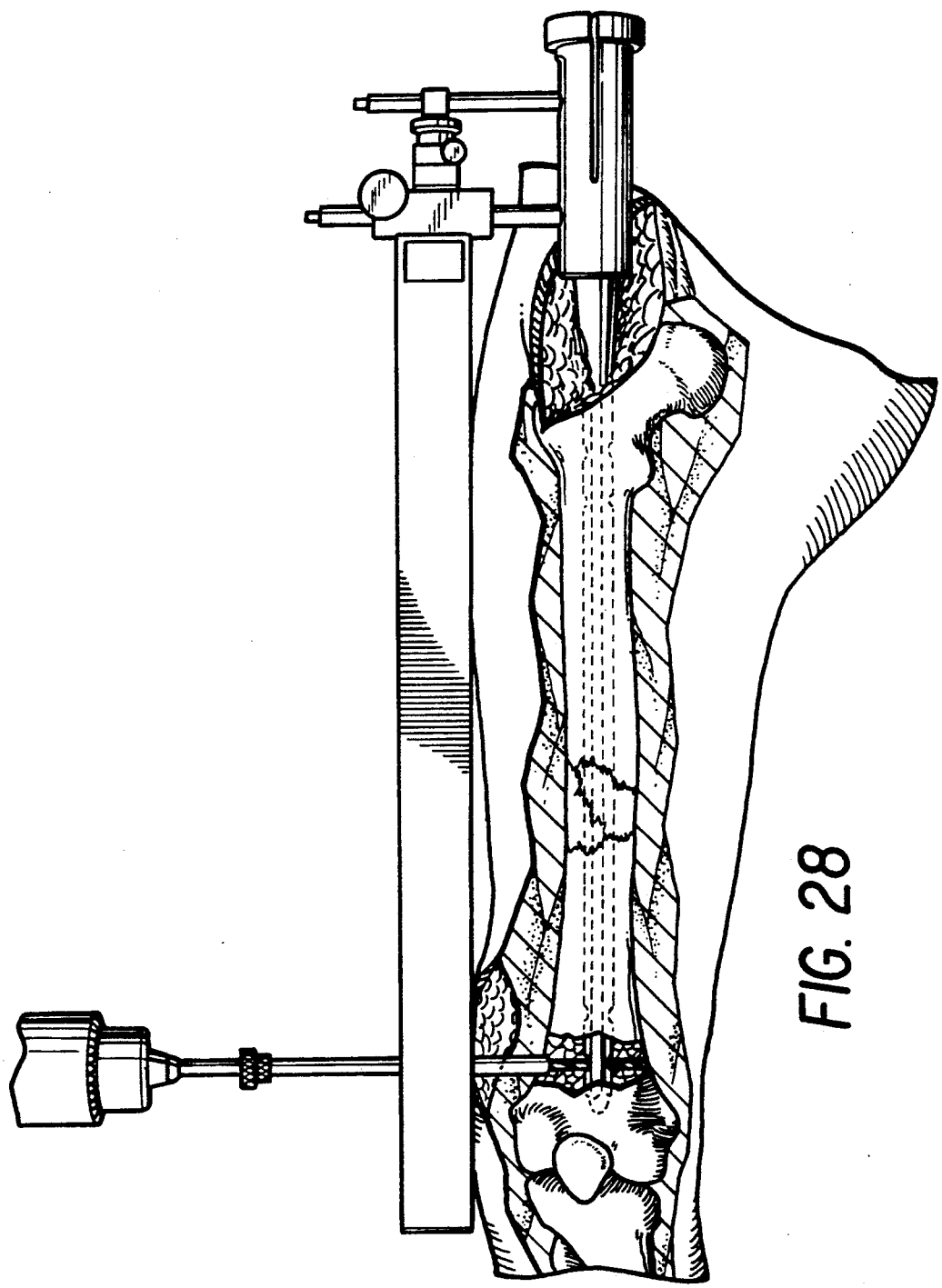
FIG. 28 illustrates drilling through both cortices.

Place the outer, serrated-end guide sleeve, drill sleeve 106 and trocar through the guide 98 and down to the lateral cortex. Lightly tap a sharp trocar to create a pilot notch as shown in FIG. 27. Be certain to keep the trocars sharp. Remove the trocar. Mount the long, ultra sharp Alta ™ 4.0 mm drill point on your power source. Insert the drill into the drill sleeve. Be absolutely certain that proper alignment is maintained. Avoid side pressure, bending, etc. Extra caution is required with heavy or cumbersome power systems. Do not use hand powered drills. Drill through both cortices as shown in FIG. 28. Verify with C-arm that the drill point is through the rod holes.

Figure 29:
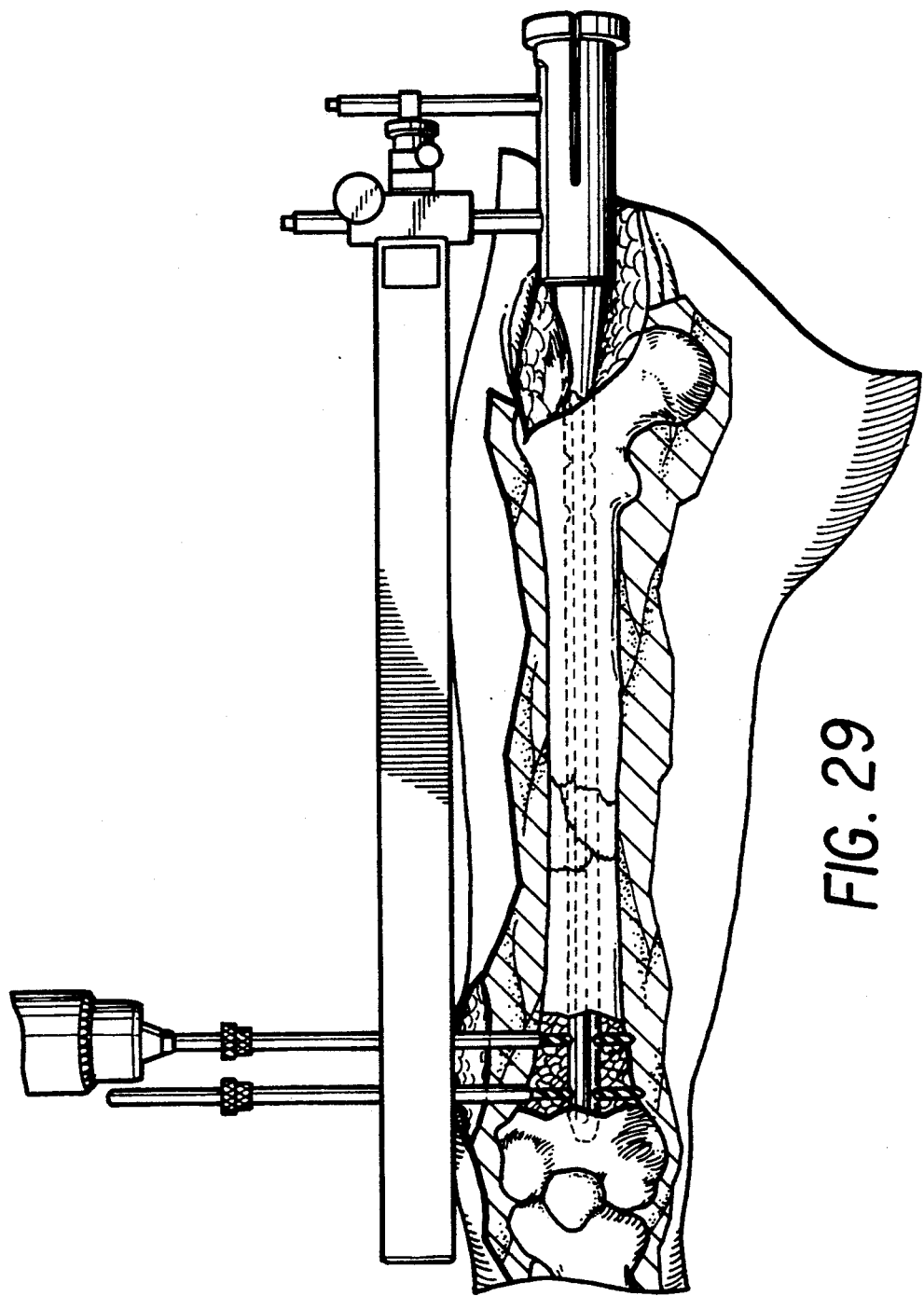
FIG. 29 illustrates both drills in position at the distal portion of the femur.

Leave the drill in place and repeat the sequence with the second distal cross-screw as shown in FIG. 29.

Figures 30, 30A:
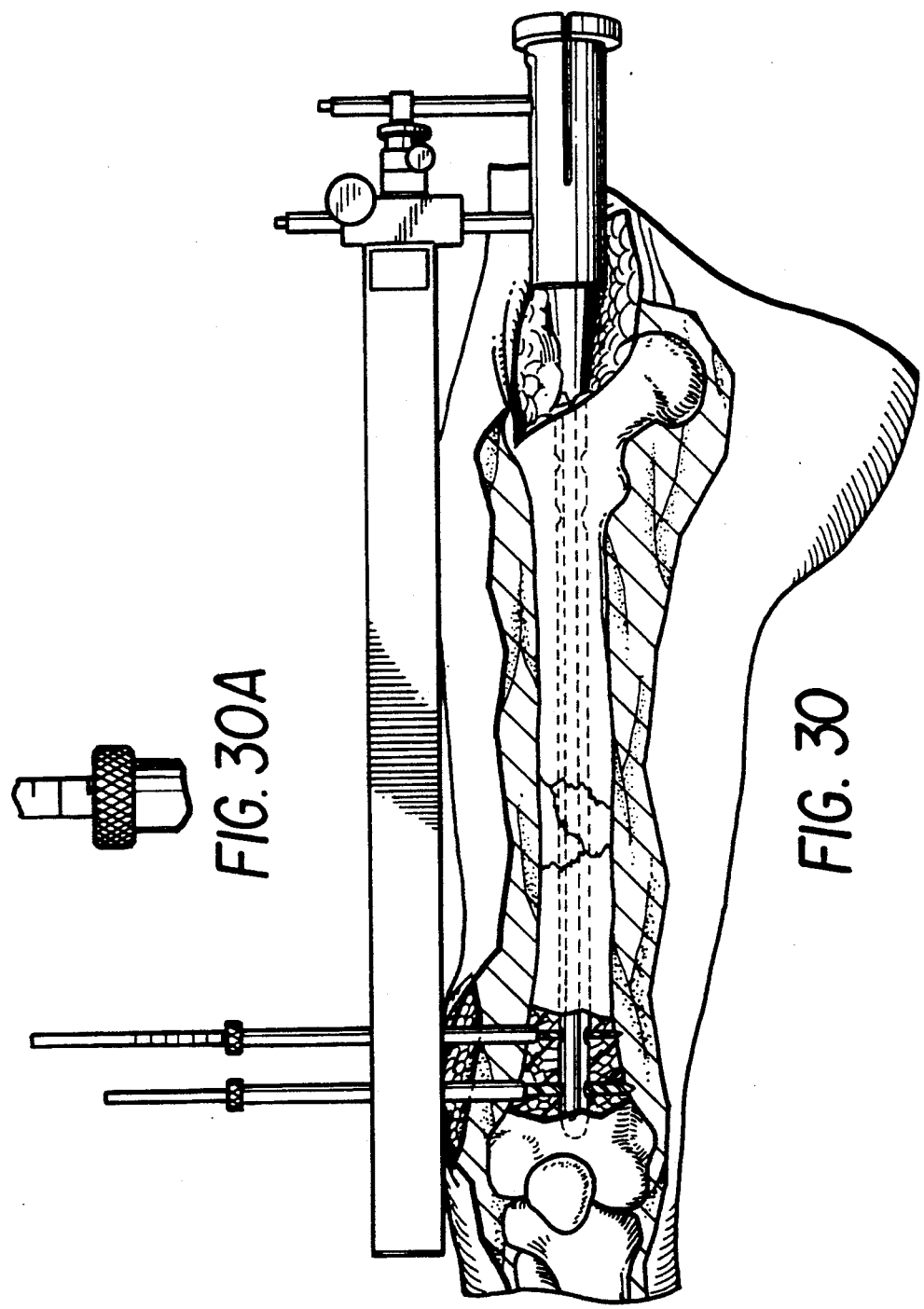
FIGS. 30 and 30A illustrates measurement of the top of the outer drill sleeve.
Figure 31:
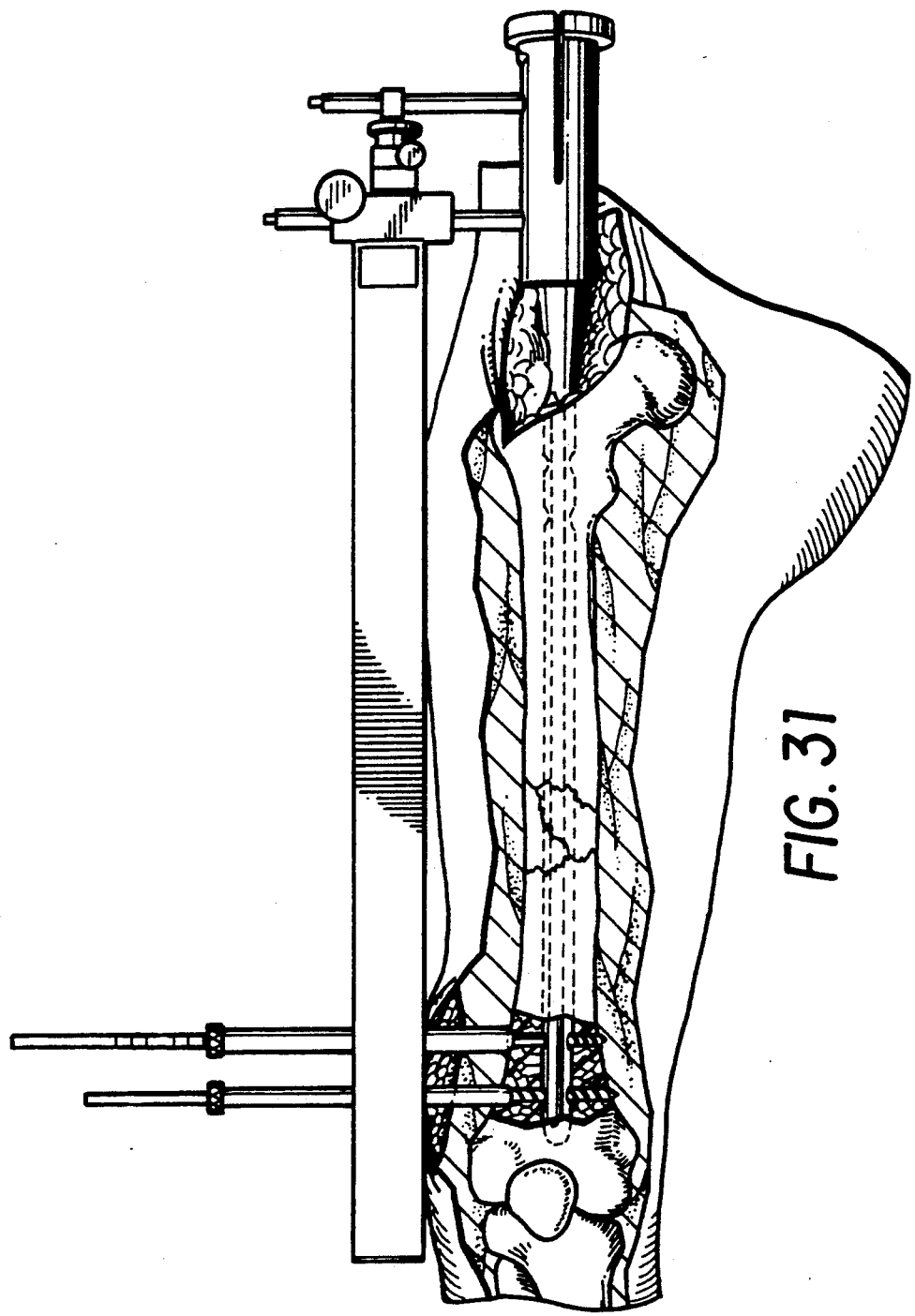
FIG. 31 illustrates placing a transverse screw through the drill sleeve.

Leaving the outer screw sleeve in place, remove the inner drill sleeve and the first drill bit. Measure for the length of the transverse screw using the crosslocking screw depth gauge. Read the measurement directly off the top of the outer drill sleeve as in FIG. 30. Overdrill through the lateral cortex using the 5 mm drill bit. Place the proper transverse screw through the screw sleeve using the long T-25 Torx ® bit as in FIG. 31. Repeat the process for the second distal cross-screw.

Figure 32:
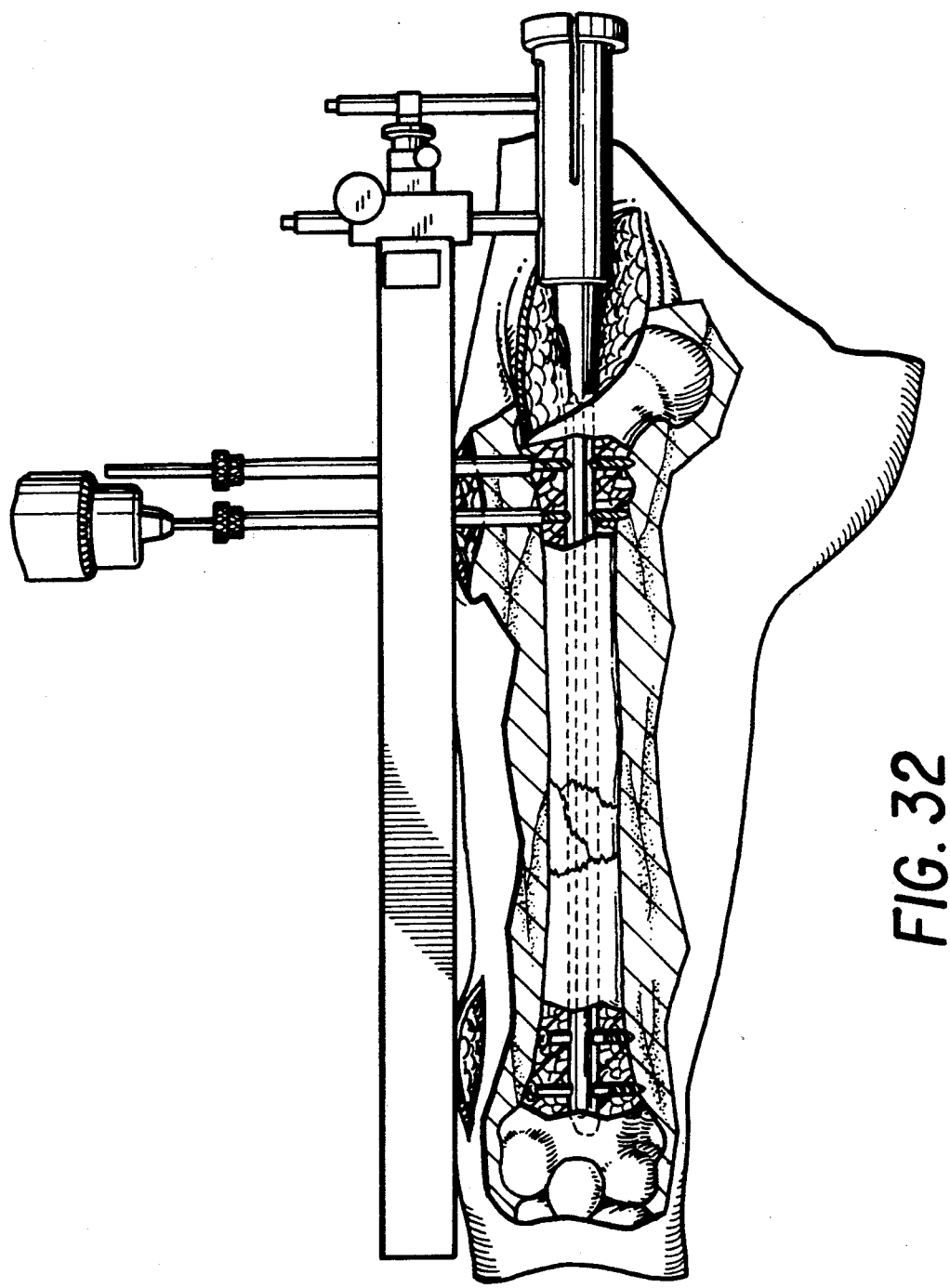
FIG. 32 illustrates drilling through the proximal end of the femur.

The proximal targeting sequence is identical to distal targeting. Again, after placing the drills through the rod 92 and both cortices, the surgeon may check radiographically to make certain that they are through the holes in the rod 92 as in FIG. 32.

Figure 33:
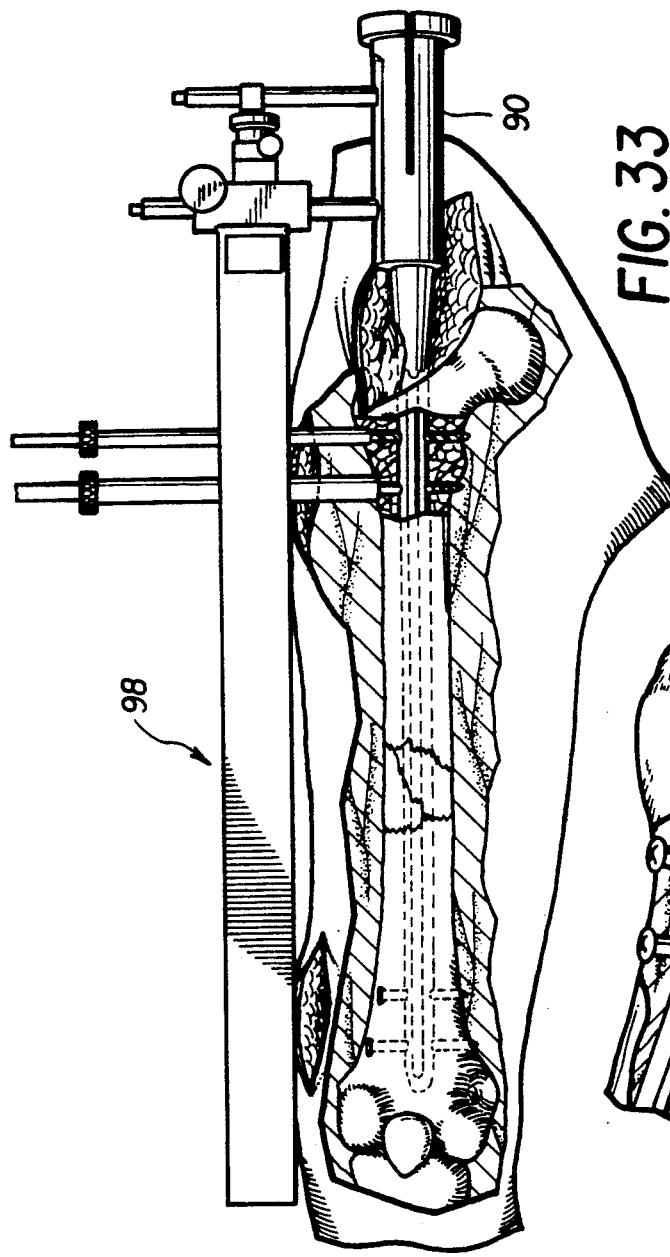
FIG. 33 illustrates placement of the proximal cross-screws.
Figure 34:
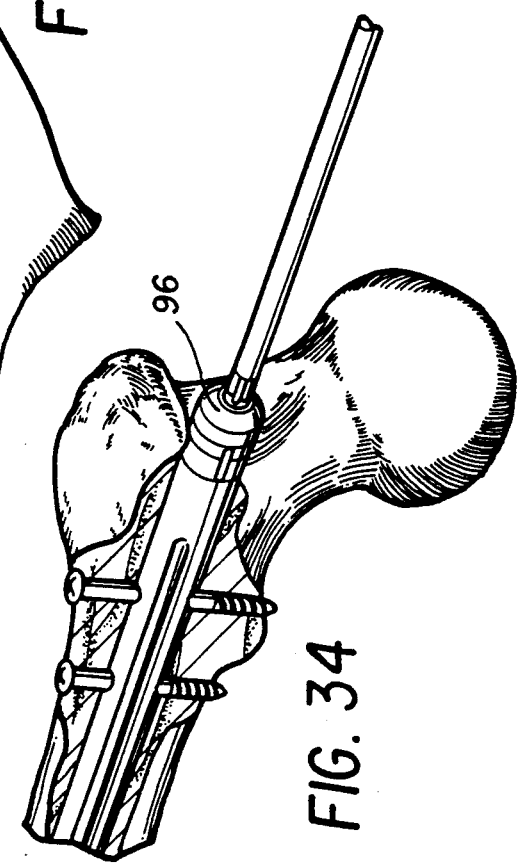
FIG. 34 illustrates placement of the rod cap screw in the top of the rod.

After placing the proximal cross-screws as in FIG. 33, remove the cross-locking guide 98 and then the driver assembly 90. Place the rod cap screw 96 in the top of the rod 92 using the T-40 Torx ® bit as shown in FIG. 34. The tip of the screw cap should be at or slightly below the tip of the greater trochanter.

Figure 35:
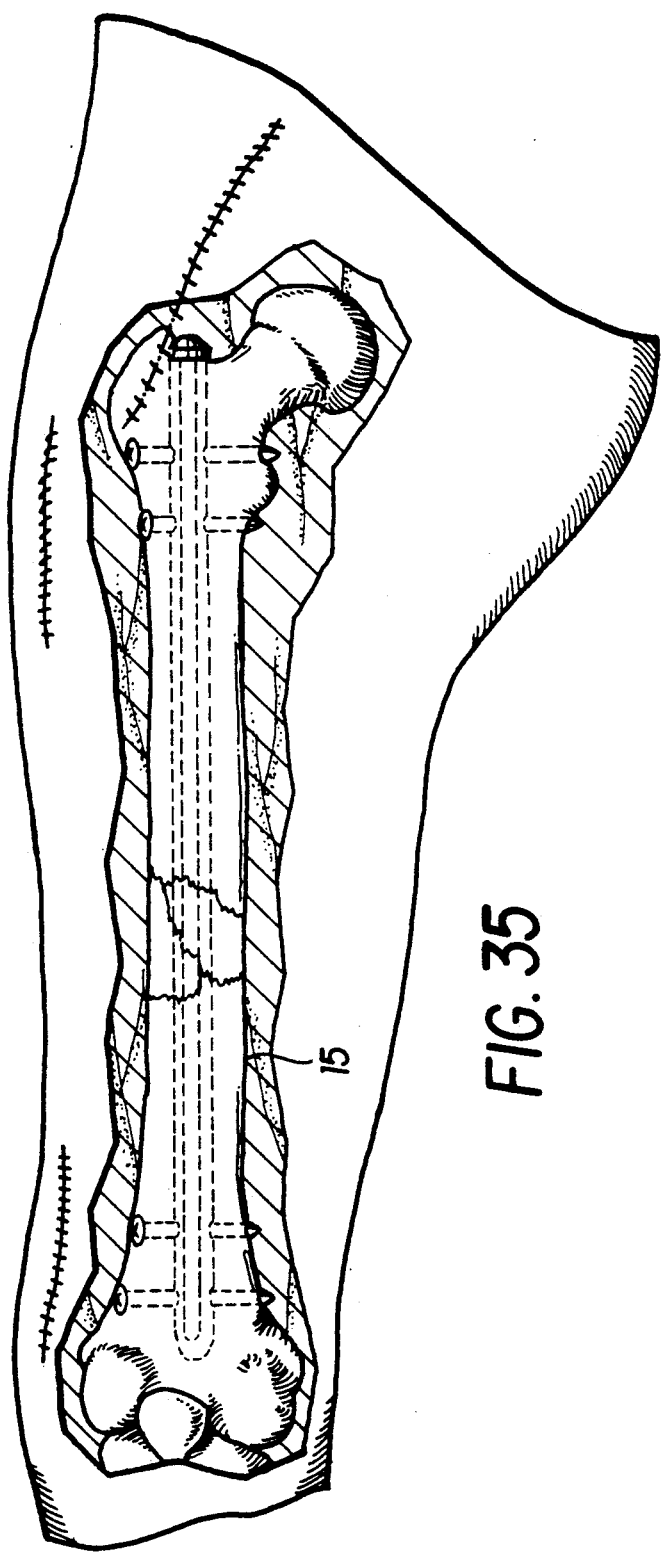
FIG. 35 illustrates reclosed wounds.

Close and dress all the wounds as in FIG. 35 and take the final radiographs.

Variations of the above-described tool 10 for reducing the fracture of a bone which involve minor changes are clearly contemplated to be within the scope of the present invention. In addition, minor variations in the design, angles or materials of the various components of the tool 10 are also contemplated to be within the scope of the present invention. These modifications and variations may be made without departing from the spirit and scope of the present invention, as will become apparent to those skilled in the art. The specific embodiments described herein are offered by way of example only, and the invention is limited only by the terms of the appended claims.

I claim:

1. Apparatus for reducing a fractured bone having a medullary canal, comprising:
   a. shaft means having distal and proximal ends and being configured and dimensioned for passage and entry of its distal end into and within the medullary canal of the fractured bone through a suitably sized aperture for manipulating into and within the medullary canal by translation and rotational movements so as to reduce the fractured bone by repositioning the various bone fragments in their proper relative arrangement, said shaft means having graduations along a portion thereof and a bore along its length; and
   b. measurement sleeve means configured and dimensioned for movement over at least the graduation portion of said shaft means outside of the medullary canal, so as to permit determination of the length of a nail to be inserted into the medullary canal of the reduced bone for fixating the fracture, said measurement sleeve means comprising a tubular sleeve movable at least along a portion of said shaft, said tubular sleeve having a body portion with extended flange ends.

2. Apparatus of claim 1 wherein said shaft means is an elongated shaft of a generally uniform diameter along its length.

3. Apparatus of claim 2 wherein said shaft is beveled at its distal end.

4. Apparatus of claim 2 wherein said shaft has graduations along a portion thereof and which cooperate with said measurement means for determination of the nail length.

5. Apparatus of claim 5 wherein said graduations are evenly spaced apart.

6. Apparatus of claim 5 wherein said graduations are in the range of thirty through forty-eight centimeters.

7. Apparatus of claim 6 wherein said graduations are spaced in one centimeter increments.

8. Apparatus of claim 4 wherein said measurement means comprises a tubular sleeve movable at least along the portion of said shaft having said graduations.

9. Apparatus of claim 8 wherein said tubular sleeve includes a window so as to permit viewing of said graduations on said shaft under said window.

10. Apparatus of claim 9 wherein said tubular sleeve has an arrow indicator positioned generally midway of said window so as to aid in measurement of the length of the nail to be inserted.

11. Apparatus of claim 10 further comprising means for selectively locking said measurement means in a predetermined position on said shaft.

12. Apparatus of claim 11 wherein said tubular sleeve further comprises a passageway communicating with the outer surface of said shaft and said measurement locking means comprises a screw dimensioned and configured for cooperative engagement with said passageway so that said screw can be advanced into said passageway and thereupon contact said outer surface so as to selectively lock said tubular sleeve in position on said shaft.

13. Apparatus of claim 2 further comprising handle means coupled to the proximal end of said shaft for aid in manipulating said shaft into and within the medullary canal, said handle means having a bore along its length aligned coaxially with said bore of said shaft.

14. Apparatus of claim 13 wherein said handle means comprises an elongated handle body which is open at one end to receive the proximal end of said shaft therein.

15. Apparatus of claim 14 further comprising chuck means for selectively securing said shaft to said handle body.

16. Apparatus of claim 15 wherein said chuck means comprises threads positioned adjacent said open end of said handle body and a collar having a bore dimensioned and configured so as to permit movement of said collar along at least the proximal end of said shaft, said collar having threads within its bore corresponding to said threads on said handle body so as to permit cooperative engagement of said first and said threads such that said open end of said handle body is selectively pressed by said collar into contact with said shaft for securement thereof.

17. Apparatus of claim 14 wherein said handle means further comprises a generally tubular handle grip positioned about a portion of said elongated handle body.

18. Apparatus of claim 17 wherein said handle means further comprises a handle rod positioned on the distal end of said handle body and extending transversely to said handle bore.

19. Apparatus for use with a guide wire for reducing a fractured bone having a medullary canal, comprising:
 a. shaft means having distal and proximal ends and being configured and dimensioned for passage and entry of its distal end into and within the medullary canal of the fractured bone through a suitably sized aperture for manipulating into and within the medullary canal by translational and rotational movements so as to reduce the fractured bone by repositioning the various bone fragments in their proper relative arrangement, said shaft means having graduations along a portion thereof and a bore along its length, said bore having a diameter greater than the general diameter of the guide wire to allow selective passage of the guide wire through said bore; and
 b. measurement sleeve means configured and dimensioned for movement over at least the graduation portion of said shaft means outside of the medullary canal, so as to permit determination of the length of a nail to be inserted into the medullary canal of the reduced bone for fixating the fracture, said measurement sleeve means comprising a tubular sleeve movable at least along a portion of said shaft, said tubular sleeve having a body portion with extended flange ends.

20. Apparatus of claim 19 further comprising handle means coupled to the proximal end of said shaft for aid in manipulating said shaft means into and within the medullary canal, said handle means having a bore along its length aligned coaxially with said bore of said shaft, said handle bore having a diameter greater than the general diameter of the guide wire to allow selective passage of the guide wire through said handle bore.

21. Apparatus of claim 20 further comprising means for selectively locking the guide wire within said handle bore in a predetermined position relative to said shaft means.

22. Apparatus for use with a guide wire for reducing a fractured femur, the guide wire being of a generally uniform diameter and having an enlarged distal end portion for placement into the medullary canal of the fractured femur, comprising:
 a. shaft means having distal and proximal ends and being configured and dimensioned for passage and entry of its distal end into and within the medullary canal of the fractured femur through a suitably sized aperture to accommodate passage of said shaft means into the medullary canal and for manipulating at least either said shaft means or the guide wire into and within the respective medullary canal portions of the fractured femur by repositioning the various bone fragments in their proper relative arrangement, said shaft means having graduations along a portion thereof and a bore along its length, said bore having a diameter greater than the diameter of the guide wire to allow selective passage of the guide wire through said bore; and
 b. measurement sleeve means configured and dimensioned for movement over at least the graduation portion of said shaft means outside of the medullary canal, so as to permit determination of the length of a nail to be inserted into the medullary canal of the reduced bone, said measurement sleeve means comprising a tubular sleeve movable at least along a portion of said shaft, said tubular sleeve having a body portion with extended flange ends.

23. Apparatus of claim 22 wherein said shaft means is a hollow elongated shaft of a generally uniform diameter along its length.

24. Apparatus of claim 23 wherein said shaft is beveled at its distal end.

25. Apparatus of claim 24 wherein said bore of said shaft is of a generally uniform diameter along its length.

26. Apparatus of claim 23 wherein said shaft has graduations along a portion thereof and which cooperate with said measurement means for determination of the nail length.

27. Apparatus of claim 26 wherein said graduations are evenly spaced apart.

28. Apparatus of claim 27 wherein said graduations are in the range of thirty through forty-eight centimeters.

29. Apparatus of claim 28 wherein said graduations are spaced in one centimeter increments.

30. Apparatus of claim 26 wherein said measurement means comprises a tubular sleeve movable at least along the portion of said shaft having said graduations.

31. Apparatus of claim 30 wherein said tubular sleeve includes a window so as to permit viewing of said graduations on said shaft under said window.

32. Apparatus of claim 31 wherein said tubular sleeve has an arrow indicator positioned generally midway of said window so as to aid in measurement of the length of the nail to be inserted.

33. Apparatus of claim 32 further comprising means for selectively locking said measurement means in a predetermined position on said shaft.

34. Apparatus of claim 33 wherein said tubular sleeve further comprises a passageway communicating with the outer surface of said shaft and said measurement locking means comprises a screw dimensioned and configured for cooperative engagement with said passageway so that said screw can be advanced into said passageway and thereupon contact said outer surface so as to selectively lock said tubular sleeve in position on said shaft.

35. Apparatus of claim 23 further comprising handle means coupled to the proximal end of said shaft for aid in manipulating said shaft into and within the medullary canal, said handle means having a bore along its length aligned coaxially with said bore of said shaft, said handle bore having a diameter greater than the general diameter of the guide wire to allow selective passage of the guide wire through said handle bore.

36. Apparatus of claim 35 wherein said handle means comprises an elongated handle body which is open at one end to receive the proximal end of said shaft therein.

37. Apparatus of claim 36 further comprising chuck means for selectively securing said shaft to said handle body.

38. Apparatus of claim 37 wherein said chuck means comprises threads positioned adjacent said open end of said handle body and a collar having a bore dimensioned and configured so as to permit movement of said collar along at least the proximal end of said shaft, said collar having threads within its bore corresponding to said threads on said handle body so as to permit cooperative engagement of said first and said threads such that said open end of said handle body is selectively pressed by said collar into contact with said shaft for securement thereof.

39. Apparatus of claim 38 wherein said handle means further comprises a generally tubular handle grip positioned about a portion of said elongated handle body.

40. Apparatus of claim 39 wherein said handle means further comprises a handle rod positioned on the distal end of said handle body and extending transversely to said second bore.

41. Apparatus of claim 40 wherein said handle grip is integrally molded about said portion of said elongated handle body.

42. Apparatus of claim 36 further comprising means for selectively locking the guide wire within said second bore in a predetermined position relative to said shaft means.

43. Apparatus of claim 41 wherein said body handle comprises a passageway communicating with and extending transversely to said second bore.

44. Apparatus of claim 43 wherein said guide wire locking means comprises a rod dimensioned for positioning in said handle body passageway and extending therefrom to a free end, said rod having a cam positioned thereon so that said cam enters into said handle bore during at least a portion of one complete rotation of said rod, said cam being configured and dimensioned so that said cam when entering said bore will contact and selectively lock the guide wire within said handle bore in position relative to said shaft.

45. Apparatus of claim 44 further comprising a knob secured to said free end of said cam rod for ease in rotating said cam rod.

46. Method for reducing a fractured bone, having a medullary canal, comprising:
   a. exposing at least a portion of the fractured bone as an entry site into the medullary canal of the fractured bone;
   b. drilling at said entry site an entry hole into the medullary canal;
   c. inserting a fracture reducing apparatus with a guide wire therein through the entry hole into and within the medullary canal, the apparatus comprising shaft means having distal and proximal ends and being configured and dimensioned for passage through said entry hole for manipulating into and within the medullary canal by translational and rotational movements so as to reduce the fractured bone, said shaft means having a bore along its length for passage of the guide wire;
   d. manipulating at least one of either said shaft means or the guide wire through the medullary canals of the fragment portions of the fractured bone so as to reduce the fracture by repositioning the various bone fragments in their proper relative arrangement;
   e. providing measurement sleeve means on said shaft means prior to insertion through said entry hole, said measurement sleeve means configured and dimensioned for movement over at least a portion of said shaft means, so as to permit determination of the length of a nail to be inserted into the medullary canal of the reduced bone, said measurement sleeve means comprising a tubular sleeve movable at least along a portion of said shaft, said tubular sleeve having a body portion with extended flange ends;

f. advancing the distal end of the guide wire generally into contact with the distal end of the medullary canal;

g. positioning said fracture reducing apparatus so that its proximal end is flush with the proximal end of the guide wire;

h. positioning said measurement means so as to abut the exposed portion of the fractured bone; and i. determining from said measurement means the length of the nail or rod to be inserted through the medullary canal for fixating the fracture.

47. Method for reducing a fractured femur having a medullary canal, comprising:

a. exposing at least a portion of the proximal end of the fractured femur as an entry site into the medullary canal of the fracture femur;

b. drilling at said entry site an entry hole into the medullary canal;

c. inserting a fracture reducing apparatus with a guide wire therein through the entry hole into and within the medullary canal, the guide wire being of a generally uniform diameter and having an enlarged distal end portion for placement into the medullary canal of the fractured femur, the apparatus comprising a hollow elongated shaft of a generally uniform diameter along its length and having distal and proximal ends and being configured and dimensioned for passage through said entry hole for manipulating into and within the medullary canal portions by translational and rotational movements so as to reduce the fractured femur, said shaft having a bore along its length for passage of the guide wire;

d. manipulating at least one of either said shaft or the guide wire through the medullary canals of the fragment portions of the fractured femur so as to reduce the fracture by repositioning the various bone fragments in their proper relative arrangement;

e. providing a measurement tubular sleeve on said shaft prior to insertion through said entry hole, said measurement tubular sleeve configured and dimensioned for movement over at least a portion of said shaft having graduations therein so as to permit determination of the length of a nail to be inserted into the medullary canal of the reduced bone, said measurement sleeve means comprising a tubular sleeve movable at least along a portion of said shaft, said tubular sleeve having a body portion with extended flange ends;

f. advancing the distal end of the guide wire generally into contact with the distal end of the medullary canal;

g. positioning said fracture reducing apparatus so that its proximal end is flush with the proximal end of the guide wire;

h. positioning said measurement tubular sleeve so as to abut the exposed portion of the fractured bone; and i. determining from said measurement tubular sleeve the length of the nail or rod to be inserted through the medullary canal for fixating the fracture.

* * * * *

UNITED STATES PATENT AND TRADEMARK OFFICE
CERTIFICATE OF CORRECTION

PATENT NO. : 5,122,146

DATED : June 16, 1992

INVENTOR(S) : Michael W. Chapman, Dana C. Mears and Charles C. Edwards

It is certified that error appears in the above-identified patent and that said Letters Patent is hereby corrected as shown below:

Column 11, line 17, claim 5, change "5" to --4--.

Signed and Sealed this

Second Day of November, 1993

Attest:

BRUCE LEHMAN

Attesting Officer

Commissioner of Patents and Trademarks